(12) United States Patent
Duplantier et al.

(10) Patent No.: US 7,235,549 B2
(45) Date of Patent: Jun. 26, 2007

(54) BENZAMIDE, HETEROARYLAMIDE AND REVERSE AMIDES

(75) Inventors: Allen J. Duplantier, Ledyard, CT (US); Chakrapani Subramanyam, South Glastonbury, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/253,112

(22) Filed: Oct. 18, 2005

(65) Prior Publication Data

US 2006/0058302 A1  Mar. 16, 2006

Related U.S. Application Data

(62) Division of application No. 10/292,887, filed on Nov. 12, 2002.

(60) Provisional application No. 60/336,781, filed on Nov. 12, 2001.

(51) Int. Cl.
   *C07D 279/16* (2006.01)
   *A61K 31/5415* (2006.01)
   *A61P 19/02* (2006.01)

(52) U.S. Cl. .................. 514/224.2; 544/52

(58) Field of Classification Search .......... 544/52; 514/224.2
   See application file for complete search history.

(56) References Cited

U.S. PATENT DOCUMENTS

| | | | |
|---|---|---|---|
| 4,594,099 A | 6/1986 | Yamada et al. | |
| 4,766,233 A | 8/1988 | Lyga | |
| 4,906,286 A | 3/1990 | Lyga | |
| 4,906,287 A | 3/1990 | Lyga et al. | |
| 5,077,409 A | 12/1991 | Wissner | |
| 5,128,351 A | 7/1992 | Wissner | |
| 5,691,376 A | 11/1997 | Caggiano et al. | |
| 5,773,646 A | 6/1998 | Chandrakumar et al. | |
| 6,020,357 A | 2/2000 | Pinto et al. | |
| 6,180,844 B1 | 1/2001 | Fujita et al. | |
| 6,187,797 B1 | 2/2001 | Pruitt et al. | |
| 6,201,024 B1 | 3/2001 | Baxter et al. | |
| 6,218,376 B1 | 4/2001 | Kindon et al. | |
| 6,258,838 B1 | 7/2001 | Baxter et al. | |
| 6,492,355 B1 | 12/2002 | Alcaraz et al. | |
| 6,927,219 B2 | 8/2005 | Duplantier | |
| 6,974,812 B2 | 12/2005 | Dombroski et al. | |
| 2003/0186981 A1 | 10/2003 | Duplantier et al. | |
| 2005/0009900 A1 | 1/2005 | Dombroski et al. | |
| 2005/0288256 A1 | 12/2005 | Li | |
| 2005/0288288 A1 | 12/2005 | Leonard et al. | |

FOREIGN PATENT DOCUMENTS

| | | |
|---|---|---|
| EP | 0 077 938 | 5/1983 |
| EP | 0 514 339 | 11/1992 |
| EP | 0 563 384 | 10/1993 |
| EP | 0 688 773 | 12/1995 |
| EP | 0 877 018 | 11/1998 |
| EP | 0 974 576 | 1/2000 |
| WO | WO 86/00072 | 1/1986 |
| WO | WO 89/02891 | 4/1989 |
| WO | WO 92/11242 | 7/1992 |
| WO | WO 93/04686 | 3/1993 |
| WO | WO 95/22532 | 8/1995 |
| WO | WO 95/27513 | 10/1995 |
| WO | WO 96/38428 | 12/1996 |
| WO | WO 97/22600 | 6/1997 |
| WO | WO 97/23212 | 7/1997 |
| WO | WO 98/28269 | 7/1998 |
| WO | WO 98/42669 | 10/1998 |
| WO | WO 98/43973 | 10/1998 |
| WO | WO 99/17777 | 4/1999 |
| WO | WO 99/29660 | 6/1999 |
| WO | WO 99/29661 | 6/1999 |
| WO | WO 99/29686 | 6/1999 |
| WO | WO 00/17190 | 3/2000 |
| WO | WO 00/27808 | 5/2000 |
| WO | WO 00/35864 | 6/2000 |
| WO | WO 00/61569 | 10/2000 |
| WO | WO 00/71509 | 11/2000 |
| WO | WO 00/71529 | 11/2000 |
| WO | WO 01/23378 | 4/2001 |
| WO | WO 01/28498 | 4/2001 |

(Continued)

OTHER PUBLICATIONS

West, Anthony R., Solid State Chemistry and its Applications, Wiley, New York, 1988, pp. 358 & 365.*

(Continued)

*Primary Examiner*—Venkataraman Balasubramanian
(74) *Attorney, Agent, or Firm*—Steven R. Eck; Todd M. Crissey; Charles W. Ashbrook

(57) ABSTRACT

The present invention relates to novel to $P2X_7$ inhibitors of formula I

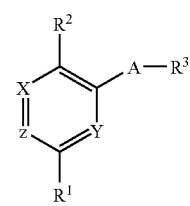

and to processes for their preparation, intermediates useful in their preparation, pharmaceutical compositions containing them, and their use in therapy. The active compounds of the present invention are potent inhibitors of $P2X_7$ and as such are useful in the treatment of inflammation, osteoarthritis, rheumatoid arthritis, cancer, reperfusion or ischemia in stroke or heart attack, autoimmune diseases and other disorders.

31 Claims, No Drawings

FOREIGN PATENT DOCUMENTS

| | | |
|---|---|---|
| WO | WO 01/42194 | 6/2001 |
| WO | WO 01/44170 | 6/2001 |
| WO | WO 01/44213 | 6/2001 |
| WO | WO 01/46200 | 6/2001 |
| WO | WO 01/58883 | 8/2001 |

OTHER PUBLICATIONS

Vippagunta et al., Advanced Drug Delivery Reviews 48: 3-26, 2001.*

Cecil Textbook of Medicine, edited by Bennet, J.C., and Plum F., 20th edition, vol. 1, 1004-1010, 1996.*

Dowd et al., British Journal of Pharmacology 125(2): 341-346, 1998.*

North et al., Current Opnion in Neurobiology, &, 346-357, 1997.*

U.S. Appl. No. 10/748,342, filed Dec. 30, 2003, Dombroski et al.

U.S. Appl. No. 11/260,075, filed Oct. 27, 2005, Dombroski et al.

U.S. Appl. No. 11/168,602, filed Jun. 28, 2005, Chung et al.

Dowd et al., "P2X receptor-mediated excitation of nociceptive afferents in the normal and arthritic rat knee joint", British Journal of Pharmacology, vol. 125, No. 2, 1998, pp. 341-346.

Theodoridis et al., "Synthesis and Structure-Activity Relationships of 1-Aryl-4-substituted-1,4-dihydro-5H-tetrazol-5-ones, a Novel Class of Pre- and Post-emergence Herbicides", Pestic. Sci., vol. 30, 1990, pp. 259-274.

Theodoridis et al., "Synthesis and Herbicidal Properties of Aryltriazolinones", American Chemical Society, Synthesis and Chemistry of Agrochemicals III, Chapter 14, 1992, pp. 134-146.

Lyga et al., "Synthesis, Herbicidal Activity, and Action Mechanism of 2-Aryl-1,2,4-triazine-3,5-diones", American Chemical Society, Synthesis and Chemistry of Agrochemicals II, Chapter 14, 1991, pp. 170-181.

International Search Report, PCT/IB02/04613, mailed Dec. 30, 2002.

* cited by examiner

BENZAMIDE, HETEROARYLAMIDE AND REVERSE AMIDES

CROSS-REFERENCE TO RELATED APPLICATIONS

This application is a division of U.S. application Ser. No. 10/292,887 filed Nov. 12, 2002, now allowed, which claims benefit of priority from U.S. provisional application No. 60/336,781 filed Nov. 12, 2001.

FIELD OF THE INVENTION

The present invention relates to novel benzamide, heteroarylamide and reverse amide, processes for their preparation, intermediates useful in their preparation, pharmaceutical compositions containing them, and their use in therapy. The active compounds of the present invention are useful in the treatment of inflammatory diseases such as osteoarthritis and rheumatoid arthritis; allergies, asthma, COPD, cancer, reperfusion or ischemia in stroke or heart attack, autoimmune diseases and other disorders. The active compounds are also antagonists of the $P2X_7$ receptor.

The $P2X_7$ receptor (previously known as P2Z receptor), which is ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis and L-selectin shedding (lymphocytes). $P2X_7$ receptors are also located on antigen-presenting cells (APC), keratinocytes, salivary acinar cells (parotid cells), hepatocytes and mesangial cells.

$P2X_7$ antagonists are known in the art, such as International Patent Publications WO 01/46200, WO 01/42194, WO 01/44213, WO 99/29660, WO 00/61569, WO 99/29661, WO 99/29686, WO 00/71529, and WO 01/44170.

Benzamides, heteroarylamides and reverse amides for uses other than inhibition of $P2X_7$ have been published, such as International Patent Publications WO 97/22600, EP 138,527, WO 00/71509, WO 98/28269, WO 99/17777 and WO 01 58883.

SUMMARY OF THE INVENTION

The present invention relates to a compound of the formula

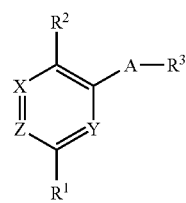

I wherein A is —(C=O)NH— or —NH(C=O)—;
X, Y and Z are =(CR$^6$)—, =(CR$^7$)—, and =(CR$^8$)—; or =N—, =(CR$^7$)—, and =(CR$^8$)—; or =(CR$^6$)—, =N—, and =(CR$^8$)—; or =(CR$^6$)—, =(CR$^7$)—, and =N—; or =N—, =(CR$^7$)—, and =N—; or =(CR$^6$)—, =N—, and =N—; or =N—, =N— and =(CR$^8$)—; respectively;

$R^1$ is a nitrogen linked $(C_1-C_{10})$heterocyclyl containing one to six heteroatoms independently selected from —N=, —N<, —NH—, —O— and —S(O)$_n$—; wherein said nitrogen linked $(C_1-C_{10})$heterocyclyl is substituted by at least one oxo group or one of said heteroatoms is —S(O)$_n$—, wherein n is one or two; wherein said nitrogen linked $(C_1-C_{10})$heterocyclyl may also optionally be substituted on any carbon atom able to support additional substituents, by one $R^9$ (preferably 1–8 $R^9$ groups per ring, more preferably 1–3 $R^9$ groups per ring), each $R^9$ is independently selected from the group of suitable substituents, such as hydrogen, halo, hydroxy, —CN, HO—$(C_1-C_4)$alkyl, $(C_1-C_4)$alkyl optionally substituted with one to three fluoro, $(C_1-C_4)$alkoxy optionally substituted with one to three fluoro, HO$_2$C—, $(C_1-C_6)$alkyl-O—(C=O)—, $R^4R^5N(O_2S)$—, $(C_1-C_4)$alkyl-$(O_2S)$—NH—, $(C_1-C_4)$alkyl-$O_2$S—$[(C_1-C_4)$alkyl-N]—, $R^4R^5N(C=O)$—, $R^4R^5N(CH_2)_t$—, $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein said nitrogen linked $(C_1-C_{10})$heterocyclyl may also optionally be substituted on any ring nitrogen atom able to support an additional substituent by one to two $R^{10}$ groups per ring, each $R^{10}$ is independently selected from the group of suitable substituents such as hydrogen, $(C_1-C_4)$alkyl optionally substituted with one to three fluoro, $(C_1-C_4)$alkyl-(C=O)—, $(C_1-C_4)$alkyl-SO$_2$—, $(C_6-C_{10})$aryl, $(C_3-C_8)$cycloalkyl, $(C_1-C_{10})$heteroaryl and $(C_1-C_{10})$heterocyclyl; wherein each of the aforesaid $(C_6-C_{10})$aryl, $(C_3-C_8)$cycloalkyl, $(C_1-C_{10})$heteroaryl and $(C_1-C_{10})$heterocyclyl anywhere on said $R^9$ and $R^{10}$ substituents may optionally be substituted on any ring carbon atom by one to three suitable moieties per ring, independently selected from the group consisting of halo, hydroxy, amino, —CN, $(C_1-C_4)$alkyl, $(C_1-C_4)$alkoxy, —CF$_3$, CF$_3$O—, $(C_1-C_4)$alkyl-NH—, $[(C_1-C_4)$alkyl]$_2$-N—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—;

n is an integer from zero to two;
q is an integer one or two;
s is an integer from one to three;
t is an integer from zero to three;
$R^2$ is chloro, bromo, $(C_1-C_4)$alkyl, —CF$_3$ or —CN;
$R^3$ is selected from the group consisting of $(C_4-C_{10})$alkyl, $(C_3-C_{12})$cycloalkyl-$(CR^{11}R^{12})_s$—, $(C_6-C_{10})$aryl-$(CR^{11}R^{12})_q$—(CH$_2$)—; $(C_1-C_{10})$heterocyclyl-$(CR^{11}R^{12})_s$— and $(C_1-C_{10})$heteroaryl-$(CR^{11}R^{12})_s$—; wherein said $(C_4-C_{10})$alkyl may optionally be independently substituted with one to three suitable substituents such as halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, $(C_1-C_4)$alkyl-(C=O)—, $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of said $R^3$ group members $(C_1-C_{10})$heterocyclyl-$(CR^{11}R^{12})_s$— and $(C_1-C_{10})$heteroaryl-$(CR^{11}R^{12})_s$— contain one to three heteroatoms independently selected from —O— and —S(O)$_n$—; wherein each of said $R^3$ group members $(C_3-C_{12})$cycloalkyl-$(CR^{11}R^{12})_s$—, $(C_6-C_{10})$aryl-$(CR^{11}R^{12})_q$—(CH$_2$)—, $(C_1-C_{10})$heterocyclyl-$(CR^{11}R^{12})_s$— and $(C_1-C_{10})$heteroaryl-$(CR^{11}R^{12})_s$— may optionally be substituted on any carbon atom able to support an additional independent suitable substituent, by one to four substituents per ring, such as halo, hydroxy, —CN, (C$_1$–C$_4$)alkyl, (C$_1$–C$_4$)alkoxy, —CF$_3$, CF$_3$O—, (C$_1$–C$_4$)alkyl-S—, (C$_1$–C$_4$)alkyl-(S═O)—, (C$_1$–C$_4$)alkyl-(SO$_2$)—, (C$_1$–C$_4$)alkyl-O—(C═O)—, formyl, (C$_1$–C$_4$)alkyl-(C═O)—, (C$_6$–C$_{10}$)aryl, (C$_3$–C$_8$)cycloalkyl, (C$_1$–C$_{10}$)heteroaryl, (C$_1$–C$_{10}$)heterocyclyl, (C$_6$–C$_{10}$)aryl-O—, benzyl-O—, (C$_3$–C$_8$)cycloalkyl-O—, (C$_1$–C$_{10}$)heteroaryl-O— and (C$_1$–C$_{10}$)heterocyclyl-O—; wherein said R$^3$ group members (C$_3$–C$_8$)cycloalkyl-(CR$^{11}$R$^{12}$)$_s$— and (C$_1$–C$_{10}$)heterocyclyl-(CR$^{11}$R$^{12}$)$_s$— may also optionally be substituted by oxo; wherein each of the aforesaid (C$_6$–C$_{10}$)aryl, (C$_3$–C$_8$)cycloalkyl, (C$_1$–C$_{10}$)heteroaryl and (C$_1$–C$_{10}$)heterocyclyl anywhere on said R$^3$ substituents may optionally be substituted on any ring carbon atom by one to three independent suitable moieties per ring, such as halo, hydroxy, amino, —CN, (C$_1$–C$_4$)alkyl, (C$_1$–C$_4$)alkoxy, —CF$_3$, CF$_3$O—, (C$_1$–C$_4$)alkyl-NH—, [(C$_1$–C$_4$)alkyl]$_2$-N—, (C$_1$–C$_4$)alkyl-S—, (C$_1$–C$_4$)alkyl-(S═O)—, (C$_1$–C$_4$)alkyl-(SO$_2$)—, (C$_1$–C$_4$)alkyl-O—(C═O)—, formyl, and (C$_1$–C$_4$)alkyl-(C═O)—;

R$^4$ and R$^5$ are each independently selected from the group consisting of hydrogen, (C$_1$–C$_6$)alkyl, HO—(C$_2$–C$_6$)alkyl and (C$_3$–C$_8$)cycloalkyl, or R$^4$ and R$^5$ may optionally be taken together with the nitrogen atom to which they are attached to form a 3 to 8 membered heterocycle;

R$^6$, R$^7$ and R$^8$ are each independently selected from the group consisting of hydrogen, halogen, cyano, hydroxyl, (C$_1$–C$_6$)alkyl optionally substituted by one to four chloro or fluoro, and (C$_1$–C$_6$)alkyloxy optionally substituted by one to four chloro or fluoro;

R$^{11}$ and R$^{12}$ are each independently selected from the group consisting of hydrogen, fluoro, cyano, hydroxyl, —CF$_3$, CF$_3$O—, (C$_1$–C$_6$)alkyl, (C$_3$–C$_8$)cycloalkyl, (C$_1$–C$_6$)alkyloxy, (C$_3$–C$_8$)cycloalkyloxy, phenyl, (C$_1$–C$_{10}$)heteroaryl and (C$_1$–C$_{10}$)heterocyclyl; wherein said (C$_1$–C$_6$)alkyl, (C$_3$–C$_8$)cycloalkyl, (C$_1$–C$_6$)alkyloxy, (C$_3$–C$_8$)cycloalkyloxy, phenyl, (C$_1$–C$_{10}$)heteroaryl and (C$_1$–C$_{10}$)heterocyclyl may optionally be substituted by one to three suitable substituents such as independently selected from chloro, fluoro, cyano, hydroxyl, —CF$_3$, CF$_3$O—, (C$_1$–C$_4$)alkyl-S—, (C$_1$–C$_4$)alkyl-(S═O)—, (C$_1$–C$_4$)alkyl-(SO$_2$)—, (C$_1$–C$_4$)alkyl-O—(C═O)—, formyl, or (C$_1$–C$_4$)alkyl-(C═O)—, with the proviso that when said R$^3$ is (C$_3$–C$_{12}$)cycloalkyl-(CR$^{11}$R$^{12}$)$_s$—; R$^1$ and R$^2$ are each hydrogen; and s is one or two; then said (C$_3$–C$_{12}$)cycloalkyl must be other than optionally substituted adamantyl;

or the pharmaceutically acceptable salts or solvates or prodrugs thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

This invention also encompasses pharmaceutical compositions containing prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

This invention also encompasses compounds of formula I containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 2nd edition, T. W. Greene and P. G. M. Wuts, Wiley-Interscience (1991).

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds. One example of a tautomeric structure is when R$^1$ is a group of the formula

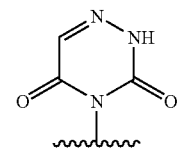

One skilled in the art will appreciate that this group can also be drawn as its tautomer

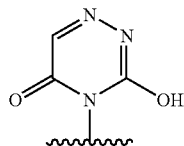

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

A "suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents.

As used herein, the term "spiro" refers to a connection between two groups, substituents etc., wherein the connection can be depicted according to the following formula

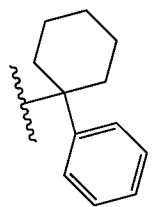

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_4)$alkyl, most preferably methyl and ethyl.

As used herein, the term "cycloalkyl" refers to a mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "halogen" includes fluoro, chloro, bromo or iodo or fluoride, chloride, bromide or iodide.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "$(C_2-C_6)$alkynyl" is used herein to mean straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e., an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "oxo" is used herein to mean a double bonded oxygen (=O) radical wherein the bond partner is a carbon atom. Such a radical can also be thought as a carbonyl group.

As used herein, the term "$(C_1-C_4)$alkyl-$O_2$S—[$(C_1-C_4)$alkyl-N]—" is used herein to mean a radical of the formula

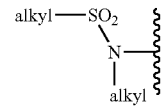

As used herein, the term "aryl" means aromatic radicals such as phenyl, naphthyl, tetrahydronaphthyl, indanyl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl. Most preferred $R^3$ heteroaryls are thienyl and furyl.

The term "heterocyclic" as used herein refers to a cyclic group containing 1–9 carbon atoms and 1 to 4 hetero atoms selected from N, O, $S(O)_n$ or NR'. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally containing 1 or 2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Preferred heterocyclics include tetrahydrofuranyl, pyrrolidinyl, piperidinyl, piperazinyl and morpholinyl. A group of $R^1$ heterocycles of particular interest are those heterocycles with 2 or more oxo substituents. Another group of $R^1$ heterocycles of particular interest are those heterocycles with three or more heteroatoms. Another group of $R^1$ heterocycles include 2-oxazepinyl, 2-oxopiperazinyl, 2-oxopiperidinyl, 2-oxopyrrolidinyl, 2-oxopyridyl and 2-oxoquinolinyl. Preferred $R^1$ heterocycles include 6-azauracil, uracil, 2-oxo-piperidine, 2,3-dioxo-piperazine, 2-oxo-oxazole and 2-oxo-benzthiazine, most preferably 6-azauracil. Preferred $R^3$ heterocyclics include tetrahydrofuranyl, dioxanyl, tetrahydrothiophenyl, chromanyl, isochromanyl and sulfolanyl.

Nitrogen heteroatoms as used herein refers to N=, >N and —NH; wherein —N= refers to a nitrogen double bond; >N refers to a nitrogen containing two bond connections and —N refers to a nitrogen containing one bond.

"Embodiment" as used herein refers to specific groupings of compounds or uses into discrete subgenera. Such subgenera may be cognizable according to one particular substituent such as a specific $R^1$ or $R^3$ group. Other subgenera are cognizable according to combinations of various substituents, such as all compounds wherein $R^2$ is chloro and $R^3$ is optionally substituted phenethyl. The phrase "in combination with each of the aforementioned embodiments" refers to combinations of the identified embodiment with each embodiment previously identified in the specification. Thus an embodiment of compounds wherein $R^3$ is optionally substituted phenethyl "in combination with each of the aforementioned embodiments" refers to additional embodiments comprising combinations of the $R^3$ is optionally substituted phenethyl embodiment with each embodiment previously identified in the specification.

A preferred embodiment of the invention is that group of phenyl compounds of formula I wherein X, Y and Z are =(CR$^6$)—, =(CR$^7$)—, and =(CR$^8$)— respectively, more preferably wherein each of R$^6$, R$^7$, and R$^8$ is hydrogen.

Another embodiment of the invention is that group of pyridyl compounds of formula I wherein X, Y and Z are =N—, =(CR$^7$)—, and =(CR$^8$)— respectively, more preferably wherein each of R$^7$ and R$^8$ is hydrogen.

Another embodiment of the invention is that group of pyridyl compounds of formula I wherein X, Y and Z are =(CR$^6$)—, =N—, and =(CR$^8$)— respectively, more preferably wherein each of R$^6$ and R$^8$ is hydrogen.

Another embodiment of the invention is that group of pyridyl compounds of formula I wherein X, Y and Z are =(CR$^6$)—, =(CR$^7$)—, and =N— respectively, more preferably wherein each of R$^6$ and R$^7$ is hydrogen.

Another embodiment of the invention is that group of pyridazine compounds of formula I wherein X, Y and Z are =N—, =(CR$^7$)—, and =N— respectively, more preferably wherein R$^7$ is hydrogen.

Another embodiment of the invention is that group of pyrimidine compounds of formula I wherein X, Y and Z are =(CR$^6$)—, =N—, and =N— respectively, more preferably wherein R$^6$ is hydrogen.

Another embodiment of the invention is that group of pyrazine compounds of formula I wherein X, Y and Z are =N—, =N—, and =(CR$^8$)— respectively, more preferably wherein R$^8$ is hydrogen.

Another more preferred embodiment of the invention is that group of amide compounds of formula I (and the phenyl, pyridyl, pyridazinyl, pyrimidyl, and pyrazinyl groups of compounds) wherein A is —(C=O)NH— and are known as the benzamide, nicotinamide, picolinamide, isonicotinamide, pyridazinamide, pyrimidinamide, and pyrazinamide groups, respectively.

Another embodiment of the invention is that group of reverse amide compounds of formula I (and the phenyl, pyridyl, pyridazinyl, pyrimidyl, and pyrazinyl groups of compounds) wherein A is —NH(C=O)— and are known as the formanilide, carboxaminopyridine, carboxaminopyridazine, carboxaminopyrimidine and carboxaminopyrazine groups, respectively.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein $R^3$ is optionally substituted $(C_4-C_{10})$alkyl, more preferably substituted with one to three substituents independently selected from hydrogen, halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein $R^3$ is optionally substituted $(C_3-C_{12})$cycloalkyl-$(CR^{11}R^{12})_s$— wherein $R^{11}$ and $R^{12}$ are each independently hydrogen or $(C_1-C_4)$alkyl or wherein at least one of $R^{11}$ and $R^{12}$ is other than hydrogen or $(C_1-C_4)$alkyl (more preferably wherein each of $R^{11}$ and $R^{12}$ of the $CR^{11}R^{12}$ directly attached to group A are hydrogen); more preferably wherein said substituents include one to three substituents independently selected from the group consisting of hydrogen, halo, hydroxy, —CN, $(C_1-C_4)$alkyl, $(C_1-C_4)$alkoxy, oxo, $(C_1-C_4)$alkyl-O—(C=O)—, formyl, $(C_1-C_4)$alkyl-(C=O)—; more preferably wherein said substituents are independently selected from the group consisting of hydrogen, halo, hydroxy, —CN, $(C_1-C_4)$alkyl and $(C_1-C_4)$alkoxy.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein $R^3$ is $(C_3-C_{12})$cycloalkyl-$(CR^{11}R^{12})_s$— (more preferably wherein each of $R^{11}$ and $R^{12}$ of the $CR^{11}R^{12}$ directly attached to group A are hydrogen) optionally substituted by at least one substituent (more preferably one substituent) selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of the aforesaid $(C_6-C_{10})$aryl, $(C_3-C_8)$cycloalkyl, $(C_1-C_{10})$heteroaryl and $(C_1-C_{10})$heterocyclyl substituents may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein $R^3$ is $(C_3-C_{12})$cycloalkyl-$(CR^{11}R^{12})_s$— (more preferably wherein each of $R^{11}$ and $R^{12}$ of the $CR^{11}R^{12}$ directly attached to group A are hydrogen) optionally substituted by at least one spiro substituent (more preferably one substituent) selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of the aforesaid $(C_6-C_{10})$aryl, $(C_3-C_8)$cycloalkyl, $(C_1-C_{10})$heteroaryl and $(C_1-C_{10})$heterocyclyl spiro substituents may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein $R^3$ is optionally substituted $(C_3-C_{12})$cycloalkyl-$(CR^{11}R^{12})_s$—;

wherein $R^{11}$ and $R^{12}$ are each independently hydrogen or $(C_1-C_4)$alkyl (more preferably wherein each of $R^{11}$ and $R^{12}$ of the $CR^{11}R^{12}$ directly attached to group A are hydrogen);

wherein said $(C_3-C_{12})$cycloalkyl of said $(C_3-C_{12})$cycloalkyl-$(CR^{11}R^{12})_s$— is substituted by one substituent selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of the aforesaid $(C_6-C_{10})$aryl, $(C_3-C_8)$cycloalkyl, $(C_1-C_{10})$heteroaryl and $(C_1-C_{10})$heterocyclyl substituents may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—; and wherein said $(C_3-C_{12})$cycloalkyl of said $(C_3-C_{12})$cycloalkyl-$(CR^{11}R^{12})_s$— is substituted by one or two substituents independently selected from the group consisting of hydrogen, halo, hydroxy, —CN, $(C_1-C_4)$alkyl, $(C_1-C_4)$alkoxy, oxo, $(C_1-C_4)$alkyl-O—(C=O)—, formyl, $(C_1-C_4)$alkyl-(C=O)—; more preferably wherein said substituents are independently selected from the group consisting of hydrogen, halo, hydroxy, —CN, $(C_1-C_4)$alkyl and $(C_1-C_4)$alkoxy.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein $R^3$ is $(C_6-C_{10})$aryl-$(CR^{11}R^{12})_q$—$(CH_2)$—; wherein $R^{11}$ and $R^{12}$ are each independently hydrogen or $(C_1-C_4)$alkyl (more preferably wherein each of $R^{11}$ and $R^{12}$ of the $CR^{11}R^{12}$ directly attached to group A are hydrogen); more preferably wherein said $(C_6-C_{10})$aryl of said $(C_6-C_{10})$aryl-$(CR^{11}R^{12})_q$—$(CH_2)$— group member is substituted by one to three substituents independently selected from the group consisting of hydrogen, halo, hydroxy, —CN, $(C_1-C_4)$alkyl, $(C_1-C_4)$alkoxy, formyl, benzyloxy and $(C_1-C_4)$alkyl-(C=O)—; more preferably wherein said $(C_6-C_{10})$aryl of said $(C_6-C_{10})$aryl-$(CR^{11}R^{12})_q$—$(CH_2)$— group member is substituted by one to three substituents independently selected from the group consisting of halo, —CN, $(C_1-C_4)$alkyl, benzyloxy and $(C_1-C_4)$alkoxy.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein $R^3$ is $(C_6-C_{10})$aryl-$(CR^{11}R^{12})_q$—$(CH_2)$—; wherein $R^{11}$ and $R^{12}$ are each independently selected from the group consisting of hydrogen or $(C_1-C_4)$alkyl (more preferably wherein each of $R^{11}$ and $R^{12}$ of the $CR^{11}R^{12}$ directly attached to group A are hydrogen); and wherein said $(C_6-C_{10})$aryl of said $(C_6-C_{10})$aryl-$(CR^{11}R^{12})_q$—$(CH_2)$— group member is substituted by at least one substituent (more preferably one substituent) selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of the aforesaid substituents may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein R$^3$ is $(C_6-C_{10})$aryl-$(CR^{11}R^{12})_q$—$(CH_2)$—; wherein R$^{11}$ and R$^{12}$ are each independently selected from the group consisting of hydrogen or $(C_1-C_4)$alkyl (more preferably wherein each of R$^{11}$ and R$^{12}$ of the CR$^{11}$R$^{12}$ directly attached to group A are hydrogen); and wherein said $(C_6-C_{10})$aryl of said $(C_6-C_{10})$aryl-$(CR^{11}R^{12})_q$—$(CH_2)$— group member is substituted by at least one spiro substituent (more preferably one substituent) selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein the aforesaid spiro substituent may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein R$^3$ is $(C_1-C_{10})$heteroaryl-$(CR^{11}R^{12})_s$— (more preferably wherein each of R$^{11}$ and R$^{12}$ of the CR$^{11}$R$^{12}$ directly attached to group A are hydrogen) optionally substituted on any ring carbon atom able to support an additional substituent by one to three substituents per ring independently selected from the group consisting of halo, hydroxy, —CN, $(C_1-C_4)$alkyl, $(C_1-C_4)$alkoxy, $(C_1-C_4)$alkyl-O(C=O)—, formyl, and $(C_1-C_4)$alkyl-(C=O)— (more preferably wherein said substituents are independently selected from the group consisting of halo, —CN, $(C_1-C_4)$alkyl, $(C_1-C_4)$alkoxy, formyl, and $(C_1-C_4)$alkyl-(C=O)—).

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein R$^3$ is $(C_1-C_{10})$heteroaryl-$(CR^{11}R^{12})_s$— (more preferably wherein each of R$^{11}$ and R$^{12}$ of the CR$^{11}$R$^{12}$ directly attached to group A are hydrogen) optionally substituted on at least one ring carbon atom able to support an additional substituent by a substituent selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein the aforesaid $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O— substituent may optionally be substituted on any ring carbon atom by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein R$^3$ is $(C_1-C_{10})$heterocyclyl-$(CR^{11}R^{12})_s$— (more preferably wherein each of R$^{11}$ and R$^{12}$ of the CR$^{11}$R$^{12}$ directly attached to group A are hydrogen) optionally substituted on any ring carbon atom (more preferably one carbon atom) able to support an additional substituent by one to three substituents per ring independently selected from the group consisting of halo, hydroxy, —CN, $(C_1-C_4)$alkyl, $(C_1-C_4)$alkoxy, oxo, $(C_1-C_4)$alkyl-O—(C=O)—, formyl, and $(C_1-C_4)$alkyl-(C=O)—(more preferably wherein said substituents are independently selected from the group consisting of halo, —CN, $(C_1-C_4)$alkyl, $(C_1-C_4)$alkoxy, oxo, formyl, and $(C_1-C_4)$alkyl-(C=O)—).

Another embodiment of the invention is that group of compounds of formula I (and the phenyl, pyridyl, pyridazinyl, pyrimidyl, and pyrazinyl groups of compounds and the benzamide, nicotinamide, picolinamide, isonicotinamide, pyridazinamide, pyrimidinamide, and pyrazinamide groups of compounds and the formanilide, carboxaminopyridine, carboxaminopyridazine, carboxaminopyrimidine and carboxaminopyrazine groups of compounds) wherein R$^3$ is $(C_1-C_{10})$heterocyclyl-$(CR^{11}R^{12})_s$— (more preferably wherein each of R$^{11}$ and R$^{12}$ of the CR$^{11}$R$^{12}$ directly attached to group A are hydrogen) optionally substituted on at least one ring carbon atom (more preferably one carbon atom) able to support an additional substituent by a substituent selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein the aforesaid $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O— substituent may optionally be substituted on any ring carbon atom by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

Another embodiment of the invention is that group of compounds wherein R$^2$ is chloro or bromo, more preferably wherein R$^2$ is chloro.

Another embodiment of the invention is that group of compounds wherein R$^2$ is $(C_1-C_4)$alkyl or —CN, more preferably wherein R$^2$ is methyl.

Another embodiment of the invention is that group of compounds wherein R$^2$ is hydroxy.

Another embodiment of the invention is that group of compounds wherein $R^7$ is other than hydrogen.

Another embodiment of the invention is that group of compounds of formula I wherein $R^1$ is optionally substituted $(C_1-C_{10})$heterocyclyl selected from the group consisting of

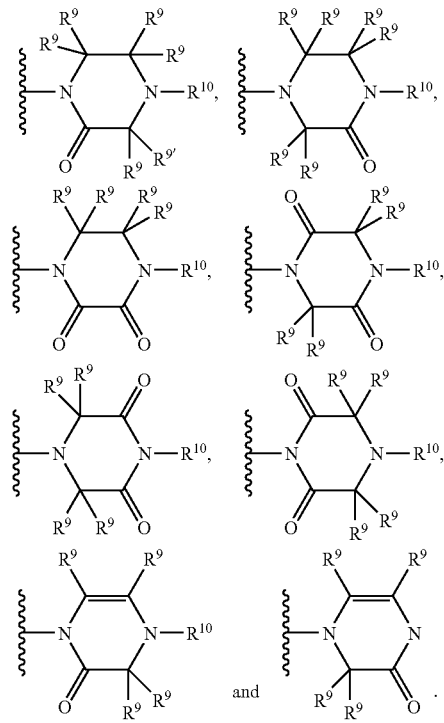

Another embodiment of the invention is that group of compounds wherein $R^1$ is optionally substituted $(C_1-C_{10})$ heterocyclyl selected from the group consisting of

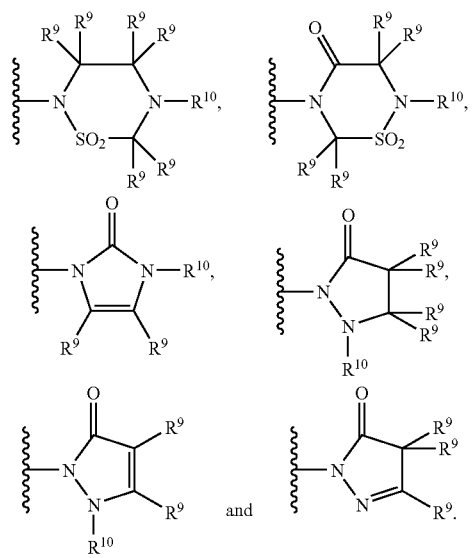

Another embodiment of the invention is that group of compounds wherein $R^1$ is optionally substituted $(C_1-C_{10})$ heterocyclyl selected from the group consisting of

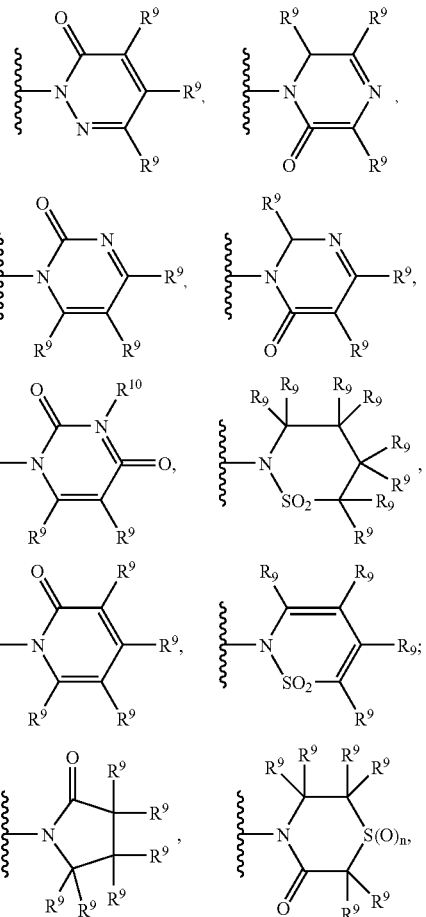

Another embodiment of the invention is that group of compounds wherein $R^1$ is optionally substituted $(C_1-C_{10})$ heterocyclyl selected from the group consisting of

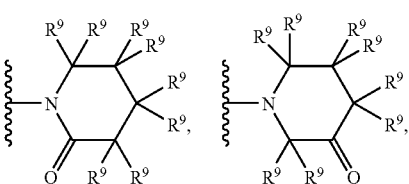

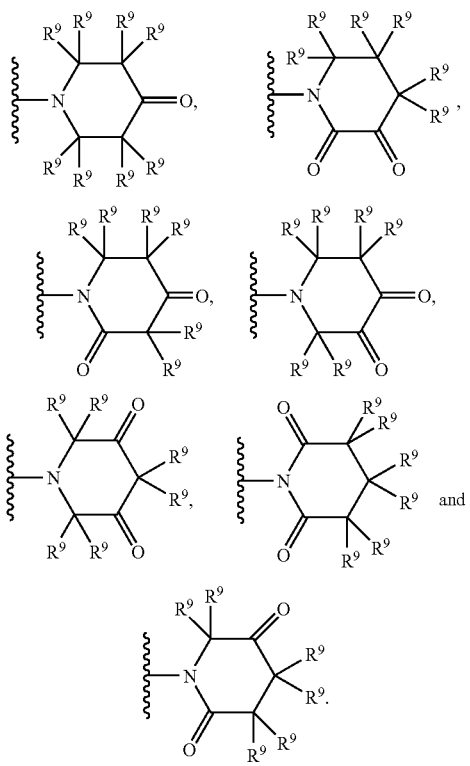

Another embodiment of the invention is that group of compounds wherein $R^1$ is optionally substituted $(C_1-C_{10})$ heterocyclyl selected from the group consisting of

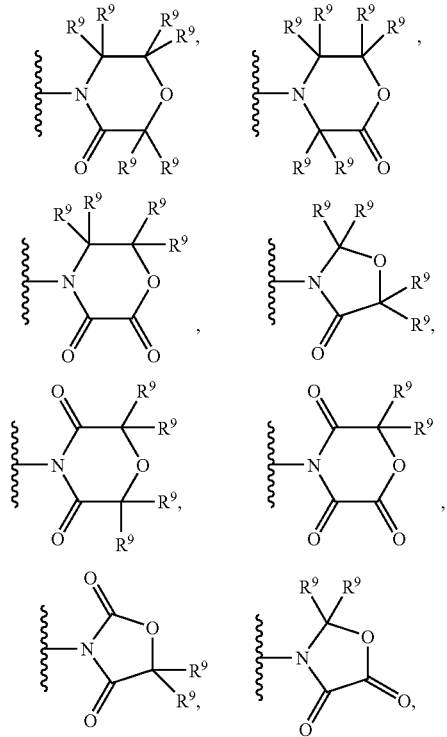

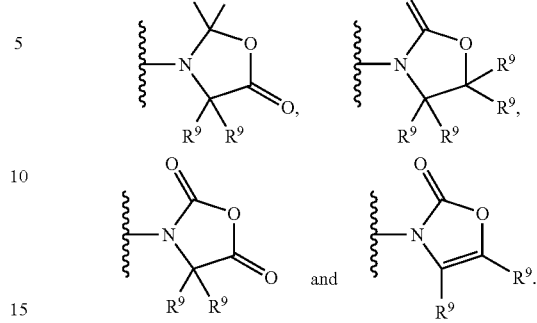

Another embodiment of the invention is that group of compounds wherein $R^1$ is optionally substituted $(C_1-C_{10})$ heterocyclyl selected from the group consisting of

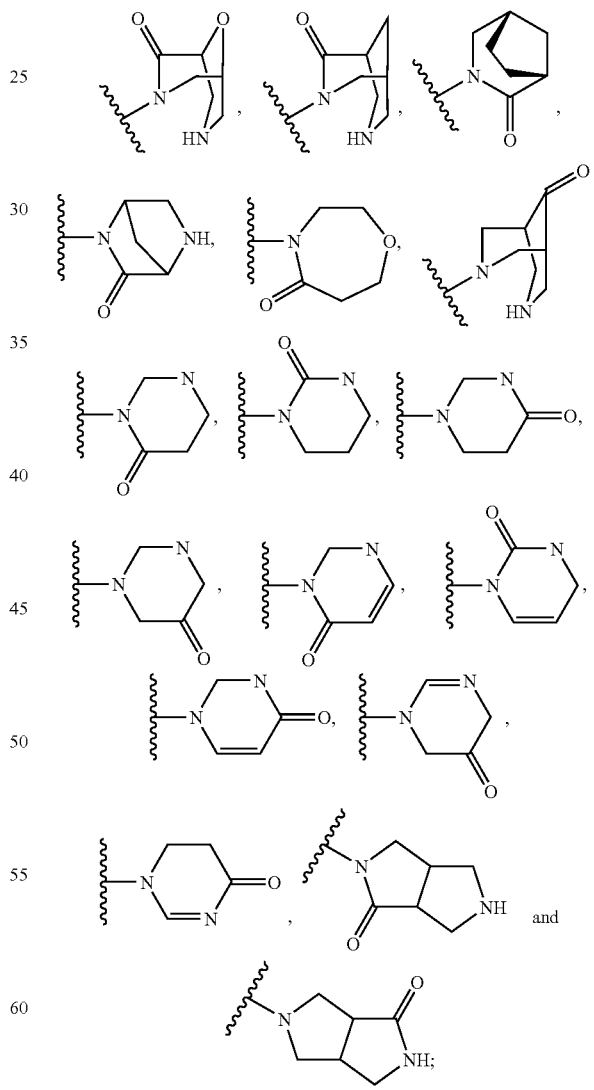

for simplicity, in the aforementioned examples of $R^1$ the substituents $R^9$ and $R^{10}$ have not been shown.

Another embodiment of the invention is that group of compounds wherein $R^1$ is optionally substituted $(C_1–C_{10})$ heterocyclyl selected from the group consisting of

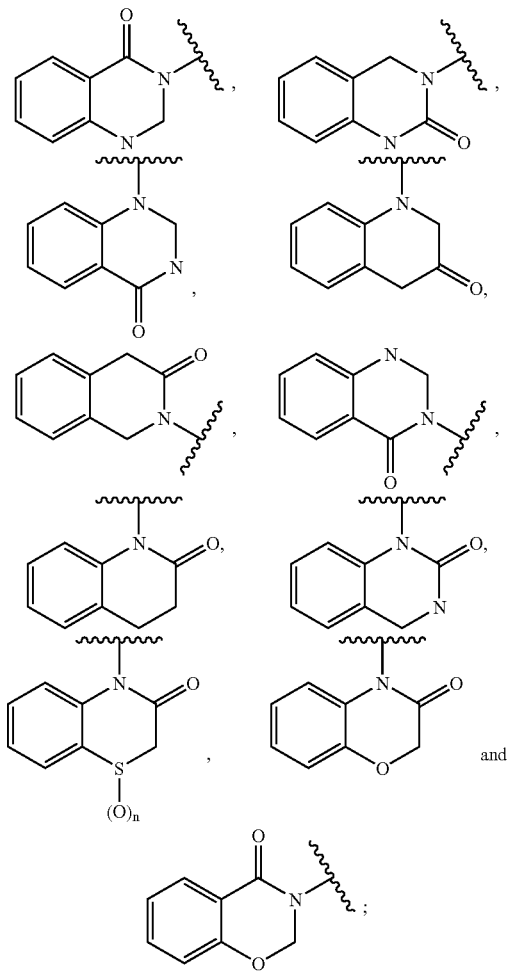

for simplicity, in the aforementioned examples of $R^1$ the substituents $R^9$ and $R^{10}$ have not been shown.

Another embodiment of the invention is that group of compounds wherein $R^1$ is optionally substituted $(C_1–C_{10})$ heterocyclyl selected from the group consisting of

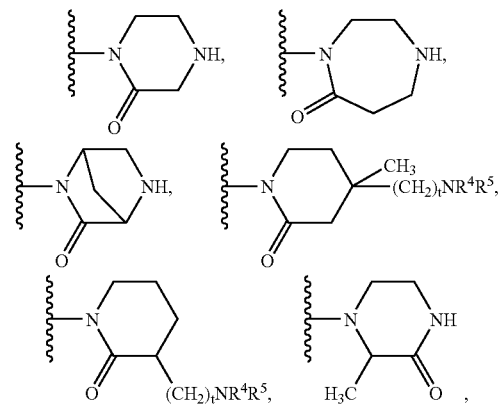

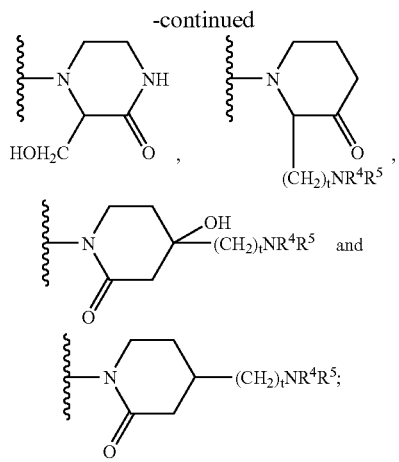

wherein $R^4$ and $R^5$ are each independently selected from the group consisting of hydrogen, $(C_1–C_6)$alkyl, HO—$(C_2–C_6)$alkyl and $(C_3–C_8)$cycloalkyl, or $R^4$ and $R^5$ may optionally be taken together with the nitrogen atom to which they are attached to form a 3 to 8 membered heterocycle.

Another embodiment of the invention is that group of compounds wherein $R^1$ is optionally substituted $(C_1–C_{10})$ heterocyclyl selected from the group consisting of

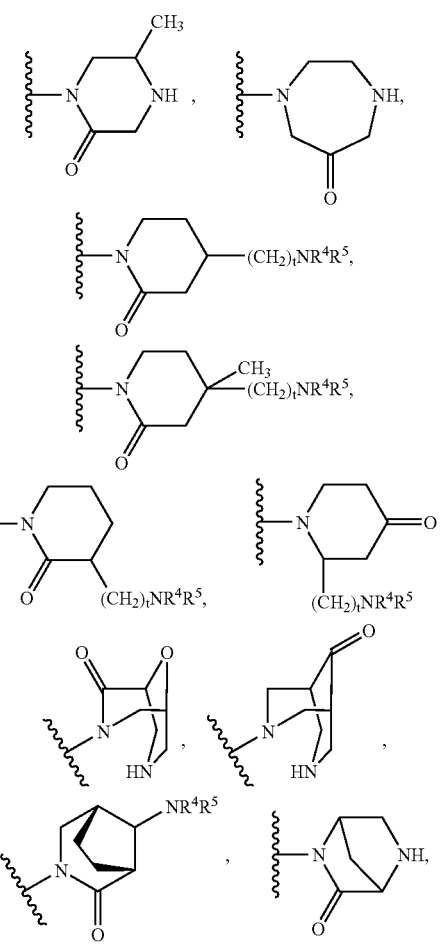

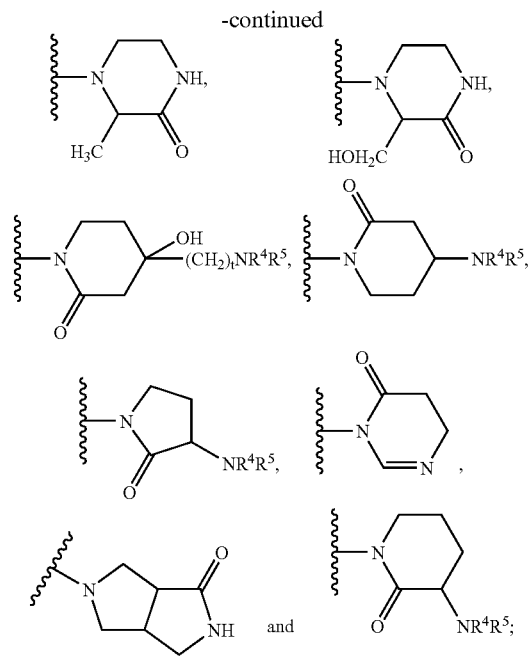

wherein $R^4$ and $R^5$ are each independently selected from the group consisting of hydrogen, $(C_1–C_6)$alkyl, HO—$(C_2–C_6)$alkyl and $(C_3–C_8)$cycloalkyl, or $R^4$ and $R^5$ may optionally be taken together with the nitrogen atom to which they are attached to form a 3 to 8 membered heterocycle.

Another embodiment of the invention is that group of compounds wherein $R^1$ is optionally substituted $(C_1–C_{10})$ heterocyclyl selected from the group consisting of

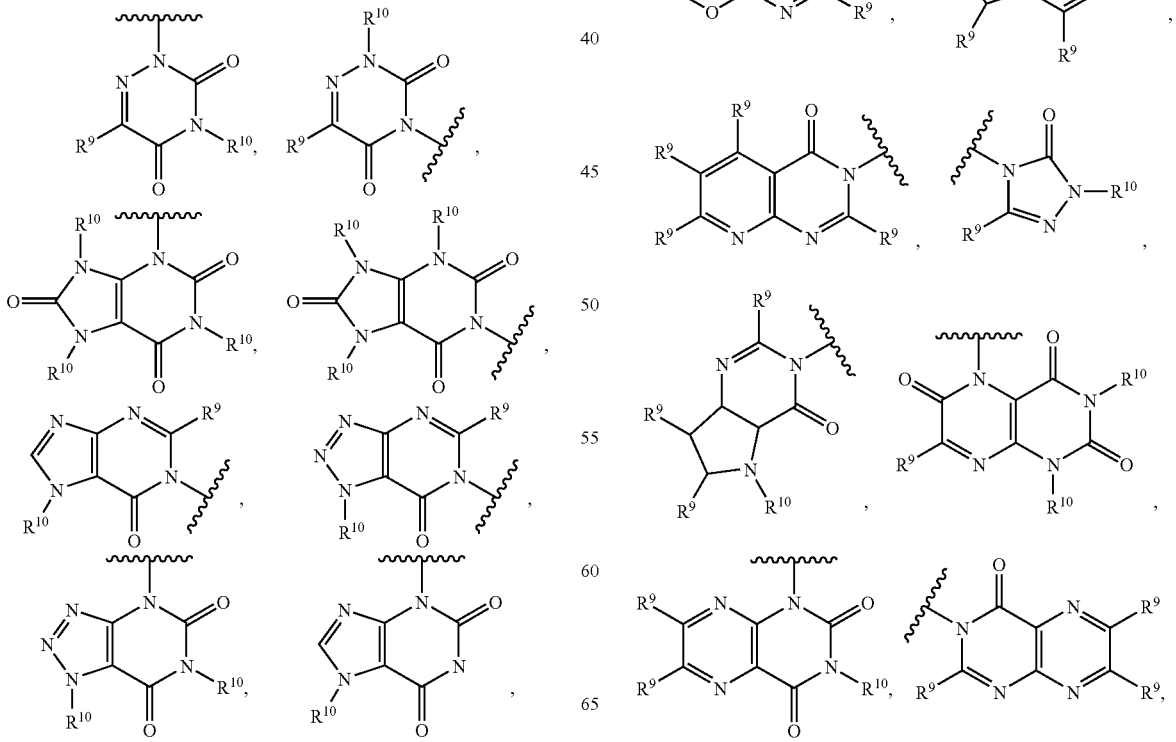

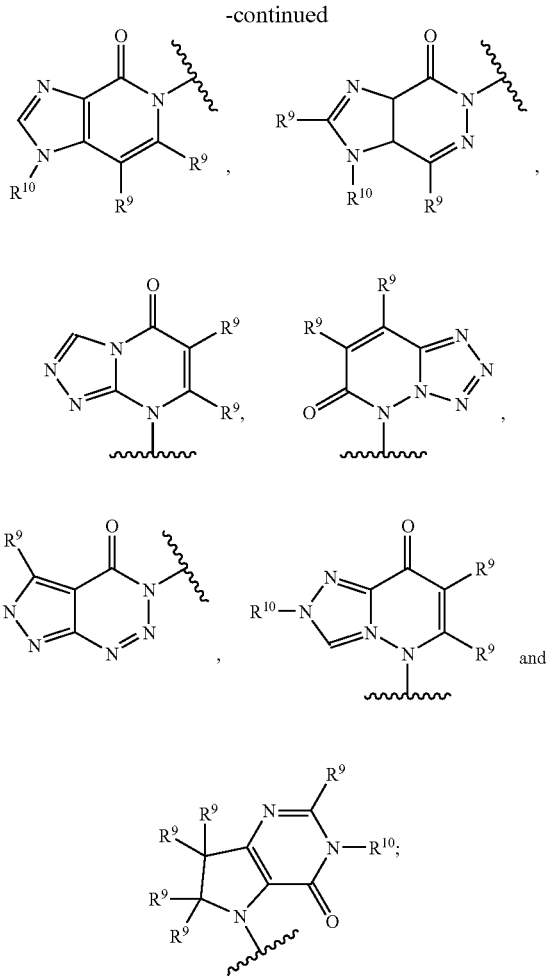

wherein R$^9$ is selected from the group consisting of hydrogen, —CF$_3$, (C$_1$–C$_6$)alkyl, HO—(C$_2$–C$_6$)alkyl and (C$_3$–C$_8$)cycloalkyl group;

wherein R$^{10}$ is selected from the group consisting of hydrogen, (C$_1$–C$_6$)alkyl, HO—(C$_2$–C$_6$)alkyl and (C$_3$–C$_8$) cycloalkyl group.

Another embodiment of the invention is that group of compounds wherein R$^9$ is independently selected from the group of substituents selected from hydrogen, halo, —CN, and (C$_1$–C$_4$)alkyl optionally substituted with one to three fluoro; more preferably hydrogen or methyl.

Another embodiment of the invention is that group of compounds wherein R$^9$ is independently selected from the group of substituents selected from hydroxy, amino, (C$_1$–C$_4$) alkoxy optionally substituted with one to three fluoro, HO$_2$C—, R$^4$R$^5$N(O$_2$S)—, (C$_1$–C$_4$)alkyl-(O$_2$S)—NH—, (C$_1$–C$_4$)alkyl-O$_2$S—[(C$_1$–C$_4$)alkyl-N]—, R$^4$R$^5$N(O═C)—, (C$_1$–C$_4$)alkyl-NH—, [(C$_1$–C$_4$)alkyl]$_2$-N— and R$^4$R$^5$N (CH$_2$)$_t$—.

Another embodiment of the invention is that group of compounds wherein each R$^9$ is independently selected from the group of substituents selected from (C$_6$–C$_{10}$)aryl, (C$_3$–C$_8$)cycloalkyl, (C$_1$–C$_{10}$)heteroaryl, (C$_1$–C$_{10}$)heterocyclyl, (C$_6$–C$_{10}$)aryl-O—, (C$_3$–C$_8$)cycloalkyl-O—, (C$_1$–C$_{10}$) heteroaryl-O— and (C$_1$–C$_{10}$)heterocyclyl-O—.

Another embodiment of the invention is that group of compounds wherein R$^{10}$ is independently selected from the group of substituents consisting of hydrogen and (C$_1$–C$_4$) alkyl optionally substituted with one to three fluoro; more preferably hydrogen or methyl.

Another embodiment of the invention is that group of compounds wherein each R$^{10}$ is independently selected from the group of substituents consisting of (C$_1$–C$_4$)alkyl-(C═O)—, (C$_6$–C$_{10}$)aryl, (C$_3$–C$_8$)cycloalkyl, wherein each of the aforesaid (C$_6$–C$_{10}$)aryl and (C$_3$–C$_8$)cycloalkyl, anywhere on said R$^{10}$ substituents may optionally be substituted by one to three suitable moieties per ring, independently selected from the group consisting of halo, hydroxy, amino, —CN, (C$_1$–C$_4$)alkyl, (C$_1$–C$_4$)alkoxy, —CF$_3$, CF$_3$O—, (C$_1$–C$_4$)alkyl-NH—, [(C$_1$–C$_4$)alkyl]$_2$-N—, (C$_1$–C$_4$)alkyl-S—, (C$_1$–C$_4$)alkyl-(S═O)—, (C$_1$–C$_4$)alkyl-(SO$_2$)—, (C$_1$–C$_4$)alkyl-O—(C═O)—, formyl, and (C$_1$–C$_4$)alkyl-(C═O)—;

Another embodiment of the invention is that group of compounds wherein each R$^{10}$ is independently selected from the group of substituents consisting of (C$_1$–C$_{10}$)heteroaryl and (C$_1$–C$_{10}$)heterocyclyl; wherein each of the aforesaid (C$_1$–C$_{10}$)heteroaryl and (C$_1$–C$_{10}$)heterocyclyl anywhere on said R$^{10}$ substituents may optionally be substituted by one to three suitable moieties per ring, independently selected from the group consisting of halo, hydroxy, amino, —CN, (C$_1$–C$_4$)alkyl, (C$_1$–C$_4$)alkoxy, —CF$_3$, CF$_3$—CH$_2$—, CF$_3$O—, (C$_1$–C$_4$)alkyl-NH—, [(C$_1$–C$_4$)alkyl]$_2$-N—, (C$_1$–C$_4$)alkyl-S—, (C$_1$–C$_4$)alkyl-(S═O)—, (C$_1$–C$_4$)alkyl-(SO$_2$)—, (C$_1$–C$_4$)alkyl-O—(C═O)—, formyl, and (C$_1$–C$_4$) alkyl-(C═O)—.

Another preferred embodiment of the invention is that group of compounds wherein R$^1$ is selected from the group

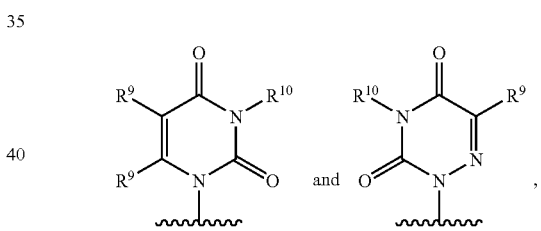

wherein R$^9$ is selected from the group consisting of hydrogen, —CF$_3$, (C$_1$–C$_6$)alkyl, HO—(C$_2$–C$_6$)alkyl or (C$_3$–C$_8$)cycloalkyl group.

wherein R$^{10}$ is selected from the group consisting of hydrogen, (C$_1$–C$_6$)alkyl, CF$_3$—CH$_2$—, HO—(C$_2$–C$_6$)alkyl or (C$_3$–C$_8$)cycloalkyl group.

A preferred embodiment of the invention relates to compounds of formula I wherein R$^1$ is

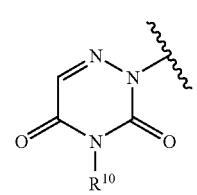

I wherein R$^{10}$ is selected from the group consisting of hydrogen, (C$_1$–C$_6$)alkyl, HO—(C$_2$–C$_6$)alkyl and (C$_3$–C$_8$) cycloalkyl group.

A more preferred embodiment of the invention relates to compounds of formula I wherein said compound of formula I has the formula

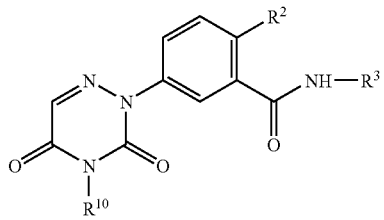

Ia wherein $R^3$ is $(C_4-C_{10})$alkyl; wherein said $(C_4-C_{10})$alkyl may optionally be substituted by one to four substituents independently selected from chloro, fluoro, $(C_6-C_{10})$aryl, $(C_3-C_6)$cycloalkyl, $(C_1-C_{10})$heteroaryl and $(C_1-C_{10})$heterocyclyl; wherein each of said $(C_6-C_{10})$aryl, $(C_3-C_8)$cycloalkyl, $(C_1-C_{10})$heteroaryl or $(C_1-C_{10})$heterocyclyl may optionally be substituted on any carbon atom able to support an additional moiety, by one to three moieties per ring, independently selected from the group consisting of halo, hydroxy, —CN, $(C_1-C_4)$alkyl, $(C_1-C_4)$alkoxy, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, $(C_1-C_4)$alkyl-(C=O)—, $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein said $(C_3-C_8)$cycloalkyl and $(C_1-C_{10})$heterocyclyl substituents may also optionally be substituted by oxo; and $R^{10}$ is hydrogen or $(C_1-C_4)$alkyl;

or a pharmaceutically acceptable salt or solvate thereof.

Another more preferred embodiment of the invention relates to compounds of formula I wherein said compound of formula I has the formula

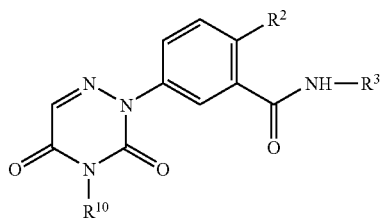

Ia wherein $R^3$ is $(C_6-C_{10})$aryl-$(CR^{11}R^{12})_q$—$(CH_2)$—; wherein said $(C_6-C_{10})$aryl may optionally be substituted by one to two substituents independently selected from the group consisting of halo, hydroxy, —CN, $(C_1-C_4)$alkyl, $(C_1-C_4)$alkoxy, $(C_1-C_4)$alkyl-O—(C=O)—, formyl, $(C_1-C_4)$alkyl-(C=O)—, $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of the aforesaid $(C_6-C_{10})$aryl, $(C_3-C_8)$cycloalkyl, $(C_1-C_{10})$heteroaryl and $(C_1-C_{10})$heterocyclyl substituents may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

or a pharmaceutically acceptable salt or solvate thereof.

Another more preferred embodiment of the invention relates to compounds of formula I wherein said compound of formula I has the formula

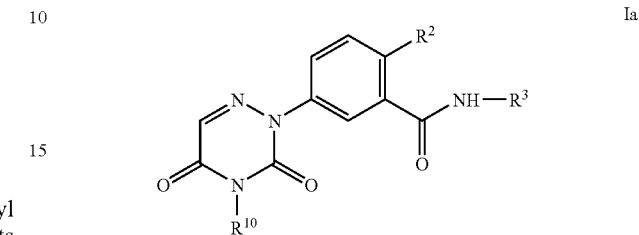

Ia wherein $R^3$ is optionally substituted $(C_3-C_{12})$cycloalkyl-$(CR^{11}R^{12})_s$— wherein $R^{11}$ and $R^{12}$ are each independently hydrogen or $(C_1-C_4)$alkyl or wherein at least one of $R^{11}$ and $R^{12}$ is other than hydrogen or $(C_1-C_4)$alkyl (more preferably wherein each of $R^{11}$ and $R^{12}$ of the $CR^{11}R^{12}$ directly attached to group A are hydrogen); halo, hydroxy, —CN, $(C_1-C_4)$alkyl, $(C_1-C_4)$alkoxy, $(C_1-C_4)$alkyl-O—(C=O)—, formyl, $(C_1-C_4)$alkyl-(C=O)—, $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of the aforesaid $(C_6-C_{10})$aryl, $(C_3-C_8)$cycloalkyl, $(C_1-C_{10})$heteroaryl and $(C_1-C_{10})$heterocyclyl substituents may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—.

Examples of specific preferred compounds of the formula I are the following:

2-Chloro-N-[2-(2-chloro-phenyl)-ethyl]-5-(3,5-dioxo-4,5-dihydro-3H-[1,2,4]triazin-2-yl)-benzamide;

2-Chloro-5-(3,5-dioxo-4,5-dihydro-3H-[1,2,4]triazin-2-yl)-N-[2-(2-fluoro-phenyl)-ethyl]-benzamide;

2-Chloro-5-(3,5-dioxo-4,5-dihydro-3H-[1,2,4]triazin-2-yl)-N-(2,2-diphenyl-ethyl)-benzamide;

N-[2-(2-Chloro-phenyl)-ethyl]-5-(3,5-dioxo-4,5-dihydro-3H-[1,2,4]triazin-2-yl)-2-methyl-benzamide;

N-[2-(2-Benzyloxy-phenyl)-ethyl]-2-chloro-5-(3,5-dioxo-4,5-dihydro-3H-[1,2,4]triazin-2-yl)-benzamide;

2-Chloro-5-(3,5-dioxo-4,5-dihydro-3H-[1,2,4]triazin-2-yl)-N-(1-phenyl-cyclohexylmethyl)-benzamide;

2-Chloro-5-(3,5-dioxo-4,5-dihydro-3H-[1,2,4]triazin-2-yl)-N-(1-p-tolyl-cyclohexylmethyl)-benzamide;

2-Chloro-N-[2-(2-chloro-phenyl)-ethyl]-5-(4-methyl-3,5-dioxo-4,5-dihydro-3H-[1,2,4]triazin-2-yl)-benzamide;

2-Chloro-5-(3,5-dioxo-4,5-dihydro-3H-[1,2,4]triazin-2-yl)-N-[2-(2-trifluoromethyl-phenyl)-ethyl]-benzamide; and 2-Chloro-N-[2-(2-chloro-phenyl)-ethyl]-5-(3-oxo-2,3-dihydro-benzo[1,4]thiazin-4-yl)-benzamide.

Examples of other compounds of the formula I are the following:

2-Chloro-5-(3,5-dioxo-4,5-dihydro-3H-[1,2,4]triazin-2-yl)-N-(2-ethyl-butyl)-benzamide;

2-Chloro-5-(3,5-dioxo-4,5-dihydro-3H-[1,2,4]triazin-2-yl)-N-(4-phenyl-butyl)-benzamide;

2-Chloro-N-[2-(4-chloro-phenyl)-ethyl]-5-(3,5-dioxo-4,5-dihydro-3H-[1,2,4]triazin-2-yl)-benzamide;

2-Chloro-5-(3,5-dioxo-4,5-dihydro-3H-[1,2,4]triazin-2-yl)-N-phenethyl-benzamide;
N-[2-(4-Bromo-phenyl)-ethyl]-2-chloro-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-[2-(3-fluoro-phenyl)-ethyl]-benzamide;
2-Chloro-N-[2-(2,6-dichloro-phenyl)-ethyl]-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-[2-(3-methoxy-phenyl)-ethyl]-benzamide;
2-Chloro-5-(3,5-dioxo-4,5-dihydro-3H-[1,2,4]triazin-2-yl)-N-pentyl-benzamide;
2-Chloro-5-(3,5-dioxo-4,5-dihydro-3H-[1,2,4]triazin-2-yl)-N-[2-(2-ethoxy-phenyl)-ethyl]-benzamide;
N-[2-(5-Bromo-2-methoxy-phenyl)-ethyl]-2-chloro-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-octyl-benzamide;
2-Chloro-N-[2-(3-chloro-phenyl)-ethyl]-5-(3,5-dioxo-4,5-dihydro-3H-[1,2,4]triazin-2-yl)-benzamide;
2-Chloro-N-[2-(2,4-dichloro-phenyl)-ethyl]-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-hexyl-benzamide;
2-Chloro-5-(3,5-dioxo-4,5-dihydro-3H-[1,2,4]triazin-2-yl)-N-[2-(4-fluoro-phenyl)-ethyl]-benzamide;
2-Chloro-N-cyclohexylmethyl-5-(3,5-dioxo-4,5-dihydro-3H-[1,2,4]triazin-2-yl)-benzamide;
2-Chloro-N-[2-(3,4-dichloro-phenyl)-ethyl]-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-(2-phenyl-propyl)-benzamide;
2-Chloro-5-(3,5-dioxo-4,5-dihydro-3H-[1,2,4]triazin-2-yl)-N-(2-thiophen-2-yl-ethyl)-benzamide;
2-Chloro-5-(3,5-dioxo-4,5-dihydro-3H-[1,2,4]triazin-2-yl)-N-[2-(2-methoxy-phenyl)-ethyl]-benzamide;
N-[2-(2-Bromo-4-methoxy-phenyl)-ethyl]-2-chloro-5-(3,5-dioxo-4,5-dihydro-3H-[1,2,4]triazin-2-yl)-benzamide;
2-Chloro-N-[2-(4-chloro-phenyl)-propyl]-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-(1-hydroxy-cyclohexylmethyl)-benzamide;
2-Chloro-5-(3,5-dioxo-4,5-dihydro-3H-[1,2,4]triazin-2-yl)-N-(5-hydroxy-1,3,3-trimethyl-cyclohexylmethyl)-benzamide;
N-Bicyclo[2.2.1]hept-2-ylmethyl-2-chloro-5-(3,5-dioxo-4,5-dihydro-3H-[1,2,4]triazin-2-yl)-benzamide;
3-{[2-Chloro-5-(3,5-dioxo-4,5-dihydro-3H-[1,2,4]triazin-2-yl)-benzoylamino]-methyl}-cyclohexanecarboxylic acid methyl ester;
N-Bicyclo[2.2.1]hept-2-ylmethyl-2-chloro-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-(2-m-tolyl-ethyl)-benzamide;
2-Chloro-N-[2-(3-chloro-phenyl)-2-hydroxy-ethyl]-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-[2-(3-fluoro-phenyl)-2-hydroxy-ethyl]-benzamide;
3-{2-[2-Chloro-5-(3,5-dioxo-4,5-dihydro-3H-[1,2,4]triazin-2-yl)-benzoylamino]-ethyl}-benzoic acid methyl ester;
2-Chloro-N-(6,6-dimethyl-bicyclo[3.1.1]hept-2-ylmethyl)-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-(2-hydroxy-2-phenyl-ethyl)-benzamide;
2-Chloro-5-(3,5-dioxo-4,5-dihydro-3H-[1,2,4]triazin-2-yl)-N-isochroman-1-ylmethyl-benzamide;
2-Chloro-5-(3,5-dioxo-4,5-dihydro-3H-[1,2,4]triazin-2-yl)-N-[2-(3-methylsulfanyl-phenyl)-ethyl]-benzamide;
2-Chloro-5-(3,5-dioxo-4,5-dihydro-3H-[1,2,4]triazin-2-yl)-N-(2-methoxy-2-phenyl-ethyl)-benzamide;
2-Chloro-N-(6,6-dimethyl-bicyclo[3.1.1]hept-2-ylmethyl)-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-(1-phenyl-cyclopentylmethyl)-benzamide;
2-Chloro-N-[2-(2-chloro-phenyl)-ethyl]-5-(2-oxo-piperidin-1-yl)-benzamide;
2-Chloro-N-[2-(2-chloro-phenyl)-ethyl]-5-(3-methoxy-2-oxo-2H-pyridin-1-yl)-benzamide;
2-Chloro-N-[2-(2-chloro-phenyl)-ethyl]-5-(4-ethyl-2,3-dioxo-piperazin-1-y)-benzamide;
2-Chloro-N-[2-(2-chloro-phenyl)-ethyl]-5-(2-oxo-oxazolidin-3-yl)-benzamide;
2-Chloro-N-[1-(4-chloro-phenyl)-4,4-difluoro-cyclohexylmethyl]-5-(3,5-dioxo-4,5-dihydro-3H-[1,2,4]triazin-2-yl)-benzamide;
2-Chloro-N-[3-(4-chloro-phenyl)-tetrahydro-pyran-3-ylmethyl]-5-[3,5-dioxo-4-(2,2,2-trifluoro-ethyl)-4,5-dihydro-3H-[1,2,4]triazin-2-yl]-benzamide;
2-Chloro-N-[2-(4-fluoro-phenyl)-tetrahydro-pyran-2-ylmethyl]-5-(3-methyl-5-oxo-1,5-dihydro-[1,2,4]triazol-4-yl)-benzamide;
N-[2-(4-Fluoro-phenyl)-[1,3]dioxan-2-ylmethyl]-2-methyl-5-(5-oxo-1,5-dihydro-[1,2,4]triazol-4-yl)-benzamide;
N-[2-(4-Fluoro-phenyl)-tetrahydro-pyran-2-ylmethyl]-2-methyl-5-[5-oxo-3-(2,2,2-trifluoro-ethyl)-1,5-dihydro-[1,2,4]triazol-4-yl]-benzamide;
5-(2,6-Dioxo-3,6-dihydro-2H-pyrimidin-1-yl)-N-[2-(4-fluoro-phenyl)-2-hydroxy-propyl]-2-methyl-benzamide;
N-[2-(2-Chloro-phenyl)-2-hydroxy-propyl]-5-(2,4-dioxo-3,4-dihydro-2H-pyrimidin-1-yl)-2-methyl-benzamide;
N-[2-Chloro-5-(3-methyl-2,5-dioxo-2,5-dihydro-pyrrol-1-yl)-phenyl]-3-(2-chloro-phenyl)-butyramide;
N-[2-Chloro-5-(3-oxo-2,3-dihydro-benzo[1,4]thiazin-4-yl)-phenyl]-3-(2-chloro-phenyl)-3-methyl-butyramide;
2-Chloro-N-[2-(2-chloro-phenyl)-2-methyl-propyl]-5-(3-oxo-2,3-dihydro-benzo[1,4]oxazin-4-yl)-benzamide;
2-Chloro-N-[2-(2-chloro-thiophen-3-yl)-ethyl]-5-(3-oxo-2,3-dihydro-benzo[1,4]thiazin-4-yl)-benzamide;
N-[2-(3-Chloro-thiophen-2-yl)-ethyl]-2-methyl-5-(7-methyl-3-oxo-2,3-dihydro-benzo[1,4]thiazin-4-yl)-benzamide;
2-Chloro-N-[2-(3-methyl-furan-2-yl)-ethyl]-5-(3-oxo-2,3-dihydro-[1,4]thiazin-4-yl)-benzamide;
2-Chloro-5-(2,4-dioxo-3,4-dihydro-2H-pyrimidin-1-yl)-N-(2-furan-2-yl-ethyl)-benzamide;
2-Chloro-5-(3,5-dioxo-4,5-dihydro-3H-[1,2,4]triazin-2-yl)-N-(1-hydroxy-cycloheptylmethyl)-benzamide;
2-Chloro-5-(3,5-dioxo-2,5-dihydro-3H-[1,2,4]triazin-4-yl)-N-(1-hydroxy-cycloheptylmethyl)-benzamide;
2-Chloro-N-(4,4-difluoro-1-hydroxy-cyclohexylmethyl)-5-(3,5-dioxo-4,5-dihydro-3H-[1,2,4]triazin-2-yl)-benzamide;
2-Chloro-N-[4,4-difluoro-1-(5-methyl-thiophen-2-yl)-cyclohexylmethyl]-5-(3,5-dioxo-4,5-dihydro-3H-[1,2,4]triazin-2-yl)-benzamide;
2-Chloro-5-(3,5-dioxo-4,5-dihydro-3H-[1,2,4]triazin-2-yl)-N-[2-(5-fluoro-thiophen-2-yl)-tetrahydro-pyran-2-ylmethyl]-benzamide;
2-Chloro-N-(1-hydroxy-cycloheptylmethyl)-5-(3-methyl-5-oxo-1,5-dihydro-[1,2,4]triazol-4-yl)-benzamide;
2-Chloro-N-cycloheptylmethyl-5-(5-oxo-3-trifluoromethyl-1,5-dihydro-[1,2,4]triazol-4-yl)-benzamide;

2-Chloro-5-(3-methyl-5-oxo-1,5-dihydro-[1,2,4]triazol-4-yl)-N-[2-(4-trifluoromethyl-phenyl)-[1,3]dioxan-2-ylmethyl]-benzamide;

2-Chloro-N-[2-(4-fluoro-phenyl)-[1,3]dioxan-2-ylmethyl]-5-(5-oxo-1,5-dihydro-[1,2,4]triazol-4-yl)-benzamide;

2-Chloro-N-[3-(4-fluoro-phenyl)-tetrahydro-pyran-3-ylmethyl]-5-[5-oxo-1-(2,2,2-trifluoro-ethyl)-1,5-dihydro-[1,2,4]triazol-4-yl]-benzamide;

N-[2-Chloro-5-(3-oxo-2,3-dihydro-benzo[1,4]thiazin-4-yl)-phenyl]-3-[2-(1-hydroxy-1-methyl-ethyl)-phenyl]-propionamide; and N-[2-Chloro-5-(3,5-dioxo-4,5-dihydro-3H-[1,2,4]triazin-2-yl)-phenyl]-3-[2-(1-hydroxy-1-methyl-ethyl)-phenyl]-propionamide.

Examples of specific nicotinamides of the invention include:

2-Chloro-N-[1-(4-chloro-phenyl)-4,4-difluoro-cyclohexylmethyl]-5-(3,5-dioxo-4,5-dihydro-3H-[1,2,4]triazin-2-yl)-nicotinamide;

2-Chloro-N-[3-(4-chloro-phenyl)-tetrahydro-pyran-3-ylmethyl]-5-[3,5-dioxo-4-(2,2,2-trifluoro-ethyl)-4,5-dihydro-3H-[1,2,4]triazin-2-yl]-nicotinamide;

2-Chloro-N-[2-(4-fluoro-phenyl)-tetrahydro-pyran-2-ylmethyl]-5-(3-methyl-5-oxo-1,5-dihydro-[1,2,4]triazol-4-yl)-nicotinamide;

N-[2-(4-Fluoro-phenyl)-[1,3]dioxan-2-ylmethyl]-2-methyl-5-(5-oxo-1,5-dihydro-[1,2,4]triazol-4-yl)-nicotinamide;

N-[2-(4-Fluoro-phenyl)-tetrahydro-pyran-2-ylmethyl]-2-methyl-5-[5-oxo-3-(2,2,2-trifluoro-ethyl)-1,5-dihydro-[1,2,4]triazol-4-yl]-nicotinamide;

5-(2,6-Dioxo-3,6-dihydro-2H-pyrimidin-1-yl)-N-[2-(4-fluoro-phenyl)-2-hydroxy-propyl]-2-methyl-nicotinamide;

N-[2-(2-Chloro-phenyl)-2-hydroxy-propyl]-5-(2,4-dioxo-3,4-dihydro-2H-pyrimidin-1-yl)-2-methyl-nicotinamide;

2-Chloro-N-[2-(2-chloro-phenyl)-2-methyl-propyl]-5-(3-oxo-2,3-dihydro-benzo[1,4]oxazin-4-yl)-nicotinamide;

2-Chloro-N-[2-(2-chloro-thiophen-3-yl)-ethyl]-5-(3-oxo-2,3-dihydro-benzo[1,4]thiazin-4-yl)-nicotinamide;

N-[2-(3-Chloro-thiophen-2-yl)-ethyl]-2-methyl-5-(7-methyl-3-oxo-2,3-dihydro-benzo[1,4]thiazin-4-yl)-nicotinamide;

2-Chloro-N-[2-(3-methyl-furan-2-yl)-ethyl]-5-(3-oxo-2,3-dihydro-[1,4]thiazin-4-yl)-nicotinamide;

2-Chloro-5-(2,4-dioxo-3,4-dihydro-2H-pyrimidin-1-yl)-N-(2-furan-2-yl-ethyl)-nicotinamide;

2-Chloro-5-(3,5-dioxo-4,5-dihydro-3H-[1,2,4]triazin-2-yl)-N-(1-hydroxy-cycloheptylmethyl)-nicotinamide;

2-Chloro-5-(3,5-dioxo-2,5-dihydro-3H-[1,2,4]triazin-4-yl)-N-(1-hydroxy-cycloheptylmethyl)-nicotinamide;

2-Chloro-N-(4,4-difluoro-1-hydroxy-cyclohexylmethyl)-5-(3,5-dioxo-4,5-dihydro-3H-[1,2,4]triazin-2-yl)-nicotinamide;

2-Chloro-N-[4,4-difluoro-1-(5-methyl-thiophen-2-yl)-cyclohexylmethyl]-5-(3,5-dioxo-4,5-dihydro-3H-[1,2,4]triazin-2-yl)-nicotinamide;

2-Chloro-5-(3,5-dioxo-4,5-dihydro-3H-[1,2,4]triazin-2-yl)-N-[2-(5-fluoro-thiophen-2-yl)-tetrahydro-pyran-2-ylmethyl]-nicotinamide;

2-Chloro-N-(1-hydroxy-cycloheptylmethyl)-5-(3-methyl-5-oxo-1,5-dihydro-[1,2,4]triazol-4-yl)-nicotinamide;

2-Chloro-N-cycloheptylmethyl-5-(5-oxo-3-trifluoromethyl-1,5-dihydro-[1,2,4]triazol-4-yl)-nicotinamide;

2-Chloro-5-(3-methyl-5-oxo-1,5-dihydro-[1,2,4]triazol-4-yl)-N-[2-(4-trifluoromethyl-phenyl)-[1,3]dioxan-2-ylmethyl]-nicotinamide;

2-Chloro-N-[2-(4-fluoro-phenyl)-[1,3]dioxan-2-ylmethyl]-5-(5-oxo-1,5-dihydro-[1,2,4]triazol-4-yl)-nicotinamide;

2-Chloro-N-[3-(4-fluoro-phenyl)-tetrahydro-pyran-3-ylmethyl]-5-[5-oxo-1-(2,2,2-trifluoro-ethyl)-1,5-dihydro-[1,2,4]triazol-4-yl]-nicotinamide;

2-Chloro-N-[2-(2-chloro-phenyl)-ethyl]-5-(3,5-dioxo-4,5-dihydro-3H-[1,2,4]triazin-2-yl)-nicotinamide;

2-Chloro-5-(3,5-dioxo-4,5-dihydro-3H-[1,2,4]triazin-2-yl)-N-[2-(2-fluoro-phenyl)-ethyl]-nicotinamide;

2-Chloro-5-(3,5-dioxo-4,5-dihydro-3H-[1,2,4]triazin-2-yl)-N-(2,2-diphenyl-ethyl)-nicotinamide;

N-[2-(2-Chloro-phenyl)-ethyl]-5-(3,5-dioxo-4,5-dihydro-3H-[1,2,4]triazin-2-yl)-2-methyl-nicotinamide;

N-[2-(2-Benzyloxy-phenyl)-ethyl]-2-chloro-5-(3,5-dioxo-4,5-dihydro-3H-[1,2,4]triazin-2-yl)-nicotinamide;

2-Chloro-5-(3,5-dioxo-4,5-dihydro-3H-[1,2,4]triazin-2-yl)-N-(1-phenyl-cyclohexylmethyl)-nicotinamide;

2-Chloro-5-(3,5-dioxo-4,5-dihydro-3H-[1,2,4]triazin-2-yl)-N-(1-p-tolyl-cyclohexylmethyl)-nicotinamide;

2-Chloro-N-[2-(2-chloro-phenyl)-ethyl]-5-(4-methyl-3,5-dioxo-4,5-dihydro-3H-[1,2,4]triazin-2-yl)-nicotinamide;

2-Chloro-5-(3,5-dioxo-4,5-dihydro-3H-[1,2,4]triazin-2-yl)-N-[2-(2-trifluoromethyl-phenyl)-ethyl]-nicotinamide; and 2-Chloro-N-[2-(2-chloro-phenyl)-ethyl]-5-(3-oxo-2,3-dihydro-benzo[1,4]thiazin-4-yl)-nicotinamide.

Examples of specific isonicotinamides of the invention include:

5-Chloro-N-[1-(4-chloro-phenyl)-4,4-difluoro-cyclohexylmethyl]-2-(3,5-dioxo-4,5-dihydro-3H-[1,2,4]triazin-2-yl)-isonicotinamide;

5-Chloro-N-[3-(4-chloro-phenyl)-tetrahydro-pyran-3-ylmethyl]-2-[3,5-dioxo-4-(2,2,2-trifluoro-ethyl)-4,5-dihydro-3H-[1,2,4]triazin-2-yl]-isonicotinamide;

5-Chloro-N-[2-(4-fluoro-phenyl)-tetrahydro-pyran-2-ylmethyl]-2-(3-methyl-5-oxo-1,5-dihydro-[1,2,4]triazol-4-yl)-isonicotinamide;

N-[2-(4-Fluoro-phenyl)-[1,3]dioxan-2-ylmethyl]-5-methyl-2-(5-oxo-1,5-dihydro-[1,2,4]triazol-4-yl)-isonicotinamide;

N-[2-(4-Fluoro-phenyl)-tetrahydro-pyran-2-ylmethyl]-5-methyl-2-[5-oxo-3-(2,2,2-trifluoro-ethyl)-1,5-dihydro-[1,2,4]triazol-4-yl]-isonicotinamide;

2-(2,6-Dioxo-3,6-dihydro-2H-pyrimidin-1-yl)-N-[2-(4-fluoro-phenyl)-2-hydroxy-propyl]-5-methyl-isonicotinamide;

N-[2-(2-Chloro-phenyl)-2-hydroxy-propyl]-2-(2,4-dioxo-3,4-dihydro-2H-pyrimidin-1-yl)-5-methyl-isonicotinamide;

5-Chloro-N-[2-(2-chloro-phenyl)-2-methyl-propyl]-2-(3-oxo-2,3-dihydro-benzo[1,4]oxazin-4-yl)-isonicotinamide;

5-Chloro-N-[2-(2-chloro-thiophen-3-yl)-ethyl]-2-(3-oxo-2,3-dihydro-benzo[1,4]thiazin-4-yl)-isonicotinamide;

N-[2-(3-Chloro-thiophen-2-yl)-ethyl]-5-methyl-2-(7-methyl-3-oxo-2,3-dihydro-benzo[1,4]thiazin-4-yl)-isonicotinamide;

5-Chloro-N-[2-(3-methyl-furan-2-yl)-ethyl]-2-(3-oxo-2,3-dihydro-[1,4]thiazin-4-yl)-isonicotinamide;

5-Chloro-2-(2,4-dioxo-3,4-dihydro-2H-pyrimidin-1-yl)-N-(2-furan-2-yl-ethyl)-isonicotinamide;

5-Chloro-2-(3,5-dioxo-4,5-dihydro-3H-[1,2,4]triazin-2-yl)-N-(1-hydroxy-cycloheptylmethyl)-isonicotinamide;

5-Chloro-2-(3,5-dioxo-2,5-dihydro-3H-[1,2,4]triazin-4-yl)-N-(1-hydroxy-cycloheptylmethyl)-isonicotinamide;

5-Chloro-N-(4,4-difluoro-1-hydroxy-cyclohexylmethyl)-2-(3,5-dioxo-4,5-dihydro-3H-[1,2,4]triazin-2-yl)-isonicotinamide;

5-Chloro-N-[4,4-difluoro-1-(5-methyl-thiophen-2-yl)-cyclohexylmethyl]-2-(3,5-dioxo-4,5-dihydro-3H-[1,2,4]triazin-2-yl)-isonicotinamide;

5-Chloro-2-(3,5-dioxo-4,5-dihydro-3H-[1,2,4]triazin-2-yl)-N-[2-(5-fluoro-thiophen-2-yl)-tetrahydro-pyran-2-ylmethyl]-isonicotinamide;

5-Chloro-N-(1-hydroxy-cycloheptylmethyl)-2-(3-methyl-5-oxo-1,5-dihydro-[1,2,4]triazol-4-yl)-isonicotinamide;

5-Chloro-N-cycloheptylmethyl-2-(5-oxo-3-trifluoromethyl-1,5-dihydro-[1,2,4]triazol-4-yl)-isonicotinamide;

5-Chloro-2-(3-methyl-5-oxo-1,5-dihydro-[1,2,4]triazol-4-yl)-N-[2-(4-trifluoromethyl-phenyl)-[1,3]dioxan-2-ylmethyl]-isonicotinamide;

5-Chloro-N-[2-(4-fluoro-phenyl)-[1,3]dioxan-2-ylmethyl]-2-(5-oxo-1,5-dihydro-[1,2,4]triazol-4-yl)-isonicotinamide;

5-Chloro-N-[3-(4-fluoro-phenyl)-tetrahydro-pyran-3-ylmethyl]-2-[5-oxo-1-(2,2,2-trifluoro-ethyl)-1,5-dihydro-[1,2,4]triazol-4-yl]-isonicotinamide;

5-Chloro-N-[2-(2-chloro-phenyl)-ethyl]-2-(3,5-dioxo-4,5-dihydro-3H-[1,2,4]triazin-2-yl)-isonicotinamide;

5-Chloro-2-(3,5-dioxo-4,5-dihydro-3H-[1,2,4]triazin-2-yl)-N-[2-(2-fluoro-phenyl)-ethyl]-isonicotinamide;

5-Chloro-2-(3,5-dioxo-4,5-dihydro-3H-[1,2,4]triazin-2-yl)-N-(2,2-diphenyl-ethyl)-isonicotinamide;

N-[2-(2-Chloro-phenyl)-ethyl]-2-(3,5-dioxo-4,5-dihydro-3H-[1,2,4]triazin-2-yl)-5-methyl-isonicotinamide;

N-[2-(2-Benzyloxy-phenyl)-ethyl]-5-chloro-2-(3,5-dioxo-4,5-dihydro-3H-[1,2,4]triazin-2-yl)-isonicotinamide;

5-Chloro-2-(3,5-dioxo-4,5-dihydro-3H-[1,2,4]triazin-2-yl)-N-(1-phenyl-cyclohexylmethyl)-isonicotinamide;

5-Chloro-2-(3,5-dioxo-4,5-dihydro-3H-[1,2,4]triazin-2-yl)-N-(1-p-tolyl-cyclohexylmethyl)-isonicotinamide;

5-Chloro-N-[2-(2-chloro-phenyl)-ethyl]-2-(4-methyl-3,5-dioxo-4,5-dihydro-3H-[1,2,4]triazin-2-yl)-isonicotinamide;

5-Chloro-2-(3,5-dioxo-4,5-dihydro-3H-[1,2,4]triazin-2-yl)-N-[2-(2-trifluoromethyl-phenyl)-ethyl]-isonicotinamide; and 5-Chloro-N-[2-(2-chloro-phenyl)-ethyl]-2-(3-oxo-2,3-dihydro-benzo[1,4]thiazin-4-yl)-isonicotinamide.

Specific examples of other pyridine-2-carboxamides include:

3-Chloro-6-(3,5-dioxo-4,5-dihydro-3H-[1,2,4]triazin-2-yl)-pyridine-2-carboxylic acid [2-(2-chloro-phenyl)-ethyl]-amide 3-Chloro-6-(3,5-dioxo-4,5-dihydro-3H-[1,2,4]triazin-2-yl)-pyridine-2-carboxylic acid (2,2-diphenyl-ethyl)-amide;

6-(3,5-dioxo-4,5-dihydro-3H-[1,2,4]triazin-2-yl)-3-methyl-pyridine-2-carboxylic acid [2-(2-Chloro-phenyl)-ethyl]-amide;

3-chloro-6-(3,5-dioxo-4,5-dihydro-3H-[1,2,4]triazin-2-yl)-pyridine-2-carboxylic acid [2-(2-Benzyloxy-phenyl)-ethyl]-amide;

3-Chloro-6-(3,5-dioxo-4,5-dihydro-3H-[1,2,4]triazin-2-yl)-pyridine-2-carboxylic acid (1-phenyl-cyclohexylmethyl)-amide;

3-Chloro-6-(3,5-dioxo-4,5-dihydro-3H-[1,2,4]triazin-2-yl)-pyridine-2-carboxylic acid (1-p-tolyl-cyclohexylmethyl)-amide;

3-Chloro-6-(4-methyl-3,5-dioxo-4,5-dihydro-3H-[1,2,4]triazin-2-yl)-pyridine-2-carboxylic acid [2-(2-chloro-phenyl)-ethyl]-amide;

3-Chloro-6-(3,5-dioxo-4,5-dihydro-3H-[1,2,4]triazin-2-yl)-pyridine-2-carboxylic acid [2-(2-trifluoromethyl-phenyl)-ethyl]-amide; and 3-Chloro-6-(3-oxo-2,3-dihydro-benzo[1,4]thiazin-4-yl)-pyridine-2-carboxylic acid [2-(2-chloro-phenyl)-ethyl]-amide.

The present invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

The compounds of Formula I or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

The present invention relates to a method for treating a P2X$_7$ mediated disease in a mammal in need thereof, which comprises administering to said mammal an effective amount of a compound of formula I.

The present invention also relates to a method for treating a condition selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic obstructive pulmonary disease, chronic pulmonary inflammatory disease, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neuro-degenerative disorders, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune disorders, Huntington's disease, diabetes, AIDS, cachexia, sepsis, septic shock, endotoxic shock, conjunctivitis shock, gram negative sepsis, toxic shock syndrome, cerebral malaria, cardiac and renal reperfusion injury, thrombosis, glomerularonephritis, graft vs. host reaction, allograft rejection, organ transplant toxicity, ulcerative colitis, or muscle degeneration, in a mammal, including a human, comprising administering to said mammal an amount of a compound to formula I, effective in treating such a condition.

The present invention relates to a pharmaceutical composition for the treatment of a P2X$_7$ mediated disease in a mammal which comprises an effective amount of a compound according to formula I and a pharmaceutically acceptable carrier.

The present invention relates to a pharmaceutical composition for the treatment of a condition selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis, chronic obstructive pulmonary disease, chronic pulmonary inflammatory disease, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neuro-degenerative disorders, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune disorders, Huntington's disease, diabetes, AIDS, cachexia, sepsis, septic shock, endotoxic shock, conjunctivitis shock, gram negative sepsis, toxic shock syndrome, cerebral malaria, cardiac and renal reperfusion injury, thrombosis, glomerularonephritis, graft vs. host reaction, allograft rejection, organ transplant toxicity, ulcerative colitis, or muscle degeneration in a mammal, including a human, comprising an amount of a compound to formula I, effective in treating such a condition and a pharmaceutically acceptable carrier.

Preferably, the compounds of the invention are useful for the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukemia, diabetes, Alzheimer's disease, meningitis, osteoporosis, burn injury, ischemic heart disease, stroke and varicose veins.

The present invention also provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

The invention further provides a method of treating osteoarthritis which comprises administering a therapeutically effective amount of a compound of formula (I), or a pharmaceutically acceptable salt or solvate thereof, as hereinbefore defined to a patient.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

The invention also provides a method of treating an obstructive airways disease (e.g. asthma or COPD) which comprises administering to a patient a therapeutically effective amount of a compound of formula (I), or a pharmaceutically acceptable salt or solvate thereof, as hereinbefore defined to a patient.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 1 mg to 1 gram, preferably 1 mg to 250 mg, more preferably 10 mg to 100 mg.

The present invention also encompasses sustained release compositions.

The present invention also relates to processes of preparing the compounds of formula I and intermediates used in such processes.

One embodiment of the processes of the invention relates to the preparation of compounds of formula

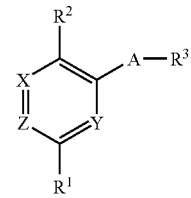

I wherein A, X, Y, Z, R$^1$, R$^2$ and R$^3$ are as described above (including all embodiments and preferences of formula I described above); comprising reacting:

a) a compound of formula

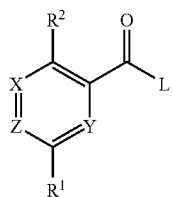

wherein X, Y, Z, R¹ and R² are as defined above; L is halo or anhydro, with a compound of the formula

wherein R³ is as defined above; and a base; or b) a compound of the formula

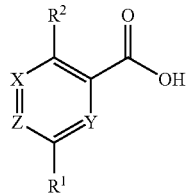

wherein X, Y, Z, R¹ and R² are as described above; with a compound of formula

wherein R³ is as defined above; in the presence of a coupling reagent, a base and a solvent; or c) a compound of the formula

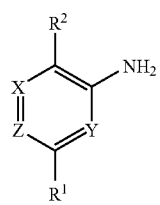

wherein X, Y, Z, R¹ and R² are as defined above; with a compound of the formula

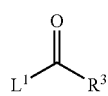

wherein L¹ is a leaving group selected from the group consisting of chloro, fluoro, bromo, iodo or anhydro, and a base and a solvent.

Another embodiment of the present invention are intermediates of the formula

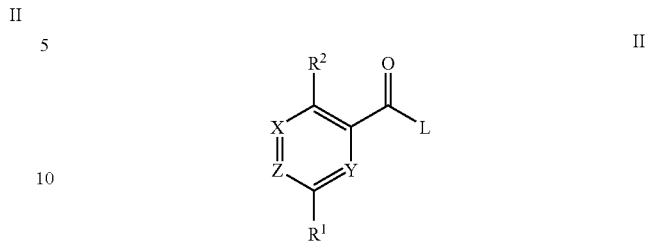

wherein X, Y, Z, R¹, R² and L are described as above (including all embodiments and preferences for X, Y, Z, R¹ and R² described above).

Another embodiment of the present invention are intermediates of the formula

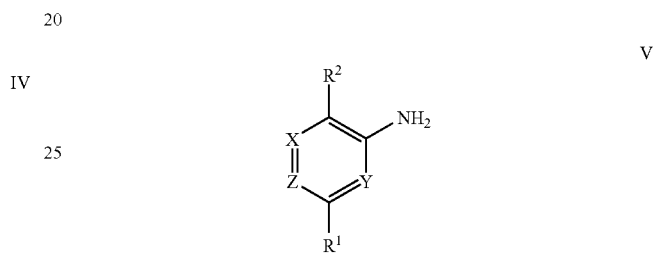

wherein X, Y, Z, R¹ and R² are as described above (including all embodiments and preferences for X, Y, Z, R¹ and R² described above).

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and $D_2E_7$) and TNF receptor immunoglobulin molecules (such as Enbrel®), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the invention together with a leukotriene biosynthesis inhibitor, 5-lipoxygenase (5-LO) inhibitor or 5-lipoxygenase activating protein (FLAP) antagonist selected from the group consisting of zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746, 530; indole and quinoline compounds such as MK-591, MK-886, and BAY x 1005.

The present invention still further relates to the combination of a compound of the invention together with a receptor antagonists for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic $H_1$ receptor antagonists including cetirizine, loratadine, desloratadine, fexofenadine, astemizole, azelastine, and chlorpheniramine.

The present invention still further relates to the combination of a compound of the invention together with a gastroprotective $H_2$ receptor antagonist.

The present invention still further relates to the combination of a compound of the invention together with an $\alpha_1$- and $\alpha_2$-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents including ipratropium bromide; tiotropium bromide; oxitropium bromide; pirenzepine; and telenzepine.

The present invention still further relates to the combination of a compound of the invention together with a $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, including prednisone, prednisolone, flunisolide, triamcinolone acetonide, beclomethasone dipropionate, budesonide, fluticasone propionate, and mometasone furoate.

The present invention still further relates to the combination of a compound of the invention together with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; (j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists selected from the group consisting of NKP-608C; SB-233412 (talnetant); and D-4418; and (t) elastase inhibitors selected from the group consisting of UT-77 and ZD-0892.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and farnesyl transferase inhibitors, VegF inhibitors, COX-2 inhibitors and antimetabolites such as methotrexate antineoplastic agents, especially antimitotic drugs including the vinca alkaloids such as vinblastine and vincristine.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

DETAILED DESCRIPTION OF THE INVENTION

Compounds of the formula I may be prepared according to the following reaction schemes and discussion. Unless otherwise indicated A, X, Y, Z, n, q, s, t, and $R^1$ through $R^{12}$ and structural formula I in the reaction schemes and discussion that follow are as defined above.

Scheme 1
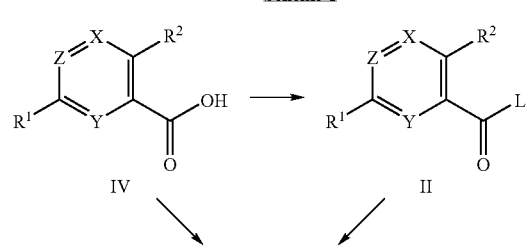
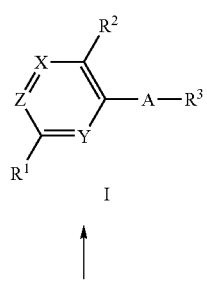
Scheme 2
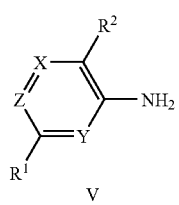
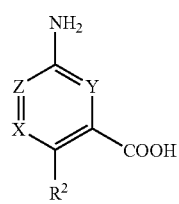
-continued
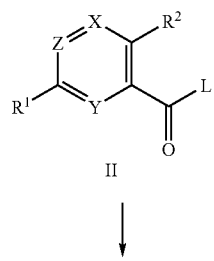
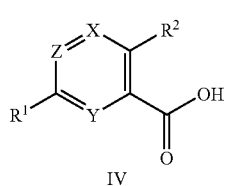
Scheme 3
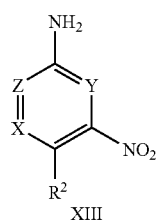

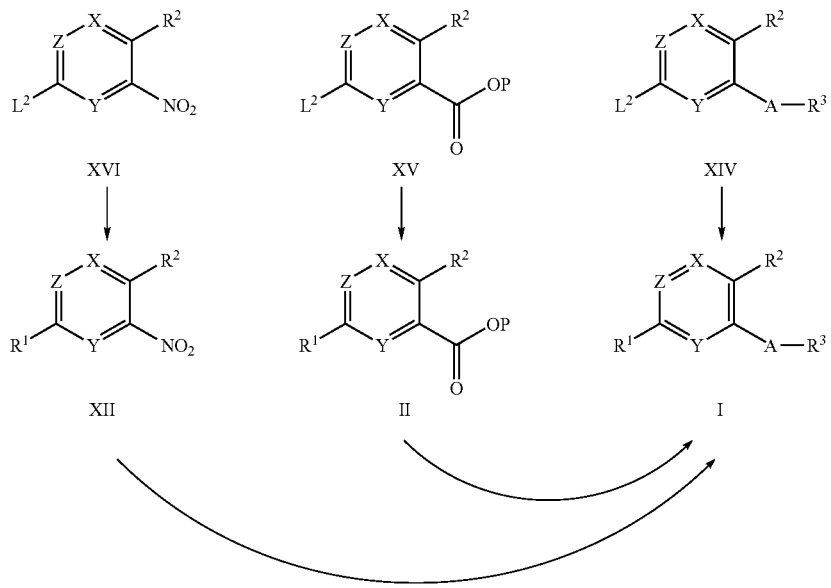

Scheme 4

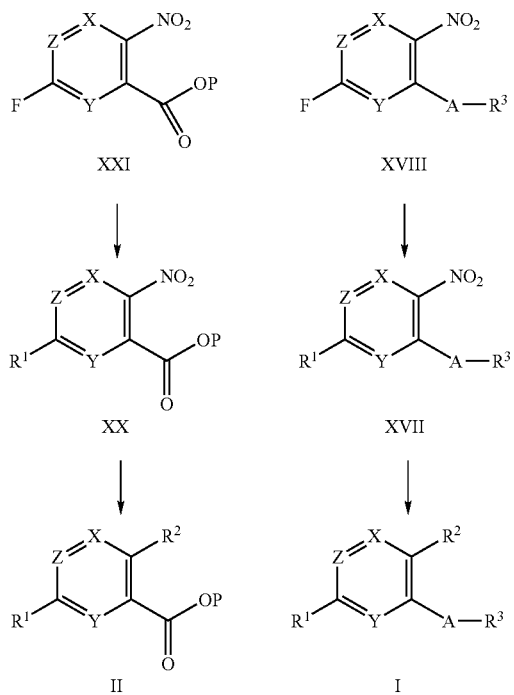

Scheme 5

Scheme 1 refers to the preparation of compounds of formula I. Compounds of formula I, wherein A is —(C=O)—NH—, can be prepared from compounds of formula II, wherein L is a halo or an anhydride leaving group of the formula R—(C=O)—O— wherein R is optionally substituted alkyl or aryl, by reaction with a compound of formula III

III in the presence of a base. Suitable bases include an excess of compound of formula III as well as triethylamine, dimethylaminopyridine, sodium carbonate, pyridine, and Hünigs base, preferably triethylamine. The aforesaid reaction may be performed neat or in the presence of a solvent. Suitable solvents include methylene chloride, tetrahydrofuran, and toluene, preferably methylene chloride.

Alternatively, compounds of formula I, wherein A is —C=ONH—, can be prepared from compounds of formula IV, by reaction with a compound of formula III in the presence of a coupling reagent, such as 1-[3-(dimethylamino)propyl]-3-ethylcarbodiimide (EDC) or dicyclohexyl carbodiimide (DCC) and hydroxybenzotriazole hydrate (HOBt), and a base, such as diisopropylethylamine (DIEA) or triethylamine, in an aprotic solvent, such as methylene chloride. Suitable solvents include methylene chloride and dimethyl formamide, preferably methylene chloride. The aforesaid reaction may be run at a temperature from about 0° C. to about 50° C., for a period from about 1 hour to about 16 hours (as illustrated in *Comprehensive Organic Transformation*, R. C. Larock, VCH Publisher, Inc. (1989) pp. 972–976).

Compounds of formula I, wherein A is —NH—(C=O)—, may be prepared from compounds of formula V by reaction with a compound of the formula VI

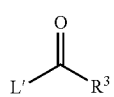

VI wherein L' is a leaving group such as chloro, fluoro, bromo, iodo or an anhydride leaving group of the formula R—(C=O)—O—, wherein R is optionally substituted alkyl or aryl. The aforesaid reaction may be conducted in the presence of a suitable base. Suitable bases include an excess of compound of formula V as well as triethylamine, dimethylaminopyridine, sodium carbonate, pyridine, and Hünigs base, preferably triethylamine. The aforesaid reaction may be performed neat or in the presence of a solvent at a temperature from about 0° C. to about 50° C., for a period from about 10 minutes to about 16 hours. Suitable solvents include methylene chloride, tetrahydrofuran, and toluene, preferably methylene chloride.

Compounds of formula II and IV can be made according to the methods of Scheme 2.

Compounds of formula V can be made according to the methods of Scheme 3.

Scheme 2 refers to the preparation of compounds of formulae IV and II, wherein L is a leaving group and $R^1$ is nitrogen linked $(C_1-C_{10})$heterocyclyl. Compounds of formulae II and IV can be converted into compounds of formula I according to the methods of Scheme 1.

Referring to Scheme 2, a compound of the formula IV can be prepared from a compound of the formula II, wherein L is a leaving group such as a methyl or ethyl ester, by reaction with a saponification reagent such as with an aqueous base, such as sodium hydroxide in an alcoholic solvent such as methanol, ethanol or tert.-butanol. The aforesaid reaction may be run at a temperature from about 0° C. to about 100° C., for a period from about 1 hour to about 24 hours. When L is a leaving group such as tert.-butyl ester, a compound of the formula IV can be prepared by the reaction of a compound of formula II with an acid such as hydrochloric acid in a solvent such as dioxane at a temperature between 25° C. to about 80° C., for a period from about 10 minutes to about 6 hours.

A compound of the formula II, wherein L is a leaving group such as alkoxy, and $R^1$ is nitrogen linked $(C_1-C_{10})$ heterocyclyl, can be prepared from a compound of the formula VII by reaction with a compound of the formula

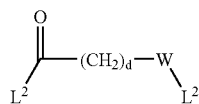

VIII wherein d is 1 to 8 and wherein any of said —$CH_2$— groups may be optionally substituted by one or two $R^9$ substituents, and wherein any of said —$CH_2$— groups may optionally be replaced with a heteroatom selected from —O—, —$S(O)_n$—, or —$NR^{10}$— wherein n is an integer from zero to 2; or any single bond between any two $CH_2$ groups may optionally be a double bond; W is >C=O or >$SO_2$; and each $L^2$ is independently hydrogen, $(C_1-C_6)$alkyl or halo; under reductive amination conditions. The reductive amination is typically carried out with a reducing agent, such as sodium cyanoborohydride or sodium triacetoxyborohydride, preferably at a pH of between 6 and 8. The reaction is normally performed in a protic solvent, such as methanol or ethanol, or in a mixture of solvents, such as dichloroethane/methanol, at temperature of about −78° C. to about 40° C. for a period from about 1 hour to about 24 hours. (See A. Abdel-Magid, C. Maryanoff, K. Carson, *Tetrahedron Lett.*, Vol. 34, Issue 31, 5595–98, 1990). Other conditions involve the use of titanium isopropoxide and sodium cyanoborohydride (R. J. Mattson et al., *J. Org. Chem.*, 1990, 55, 2552–4) or involve the formation of the imine under dehydrating conditions followed by reduction (*Comprehensive Organic Transformation*, R. C. Larock, VCH Publisher, Inc (1989) pp. 421–425).

Alternatively, a compound of the formula II, wherein L is a leaving group such as alkoxy, and $R^1$ is $(C_1-C_{10})$heterocyclyl wherein the bridgehead atom is nitrogen, can be prepared from the diazonium intermediate derived from a compound of the formula VII. The diazonium intermediate is prepared by reaction of a compound of the formula VII with an acid such as hydrochloric acid followed by treatment with sodium nitrite in a solvent such as glacial acetic acid at a temperature from about 0° C. to about 30° C., and the reaction is generally run for a period of about 30 min to about 3 hours. The compound of the formula II is prepared by the reaction of the above diazonium intermediate with a compound of the formula VIII wherein d is 1 to 8 and wherein any of said —$CH_2$— groups may be optionally substituted by one or two $R^9$ substituents, and wherein any of said —$CH_2$— groups may optionally be replaced with either an oxo group or a heteroatom selected from —O—, —$S(O)_n$—, or —$NR^{10}$— wherein n is an integer from zero to 2; or any single bond between any two $CH_2$ groups may optionally be a double bond; W is >C=O or >$SO_2$; and each $L^2$ is independently alkoxy or halo; under basic conditions. The reaction is typically carried out with sodium acetate as base at a temperature from about 0° C. to about 120° C., and the reaction is generally run for a period of about 1 hour to about 24 hours. (For example, see R. D. Carroll et al., *J. Med. Chem.*, 1983, 26, 96–100).

Alternatively, one skilled in the art will also appreciate that a compound of formula II wherein $R^1$ is a nitrogen linked $(C_1-C_{10})$heterocycle, can be prepared by standard synthetic methods from a compound of the formula VII, wherein L is a protecting group such as alkoxy, by reaction with a bidentate reagent wherein two different transformable groups exist, such as an alkylating and acylating group of the formula

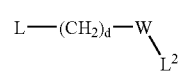

IX wherein L is a leaving group such as halo, $L^2$ is hydrogen, $(C_1-C_6)$alkyl, hydroxy, $(C_1-C_6)$alkoxy or halo; W is >C=O or >$SO_2$; d is 1 to 9 and wherein any of said —$CH_2$— groups may be optionally substituted by one or two $R^9$ substituents, and wherein any of said —$CH_2$— groups may optionally be replaced with a heteroatom selected from —O—, —$S(O)_n$—, or —$NR^{10}$— wherein n is an integer from zero to 2; or any single bond between any two $CH_2$ groups may optionally be a double bond.

Alternatively, one skilled in the art will also appreciate that a compound of formula II wherein $R^1$ is an nitrogen linked $(C_1-C_{10})$heterocycle, can be prepared by standard synthetic methods from a compound of the formula VII, wherein L is a protecting group such as alkoxy, by reaction with an anhydride reagent of the formula

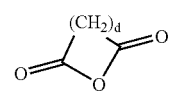

X wherein d is 1 to 9 and wherein any of said —$CH_2$— groups may be optionally substituted by one or two $R^9$ substituents, and wherein any of said —$CH_2$— groups may optionally be replaced with a heteroatom selected from —O—, —S(O)$_n$—, or —NR$^{10}$— wherein n is an integer from zero to 2; or any single bond between any two CH$_2$ groups may optionally be a double bond.

Compounds of the formula VII can be prepared from compounds of the formula XI by reaction with an alcohol of the formula ROH, wherein R is optionally substituted (C$_1$–C$_4$)alkyl or (C$_6$–C$_{10}$)aryl, in the presence of an acid (a so called Fischer esterification) or a coupling reagent, such as 1-[3-(dimethylamino)propyl]-3-ethylcarbodiimide (EDC) or dicyclohexyl carbodiimide (DCC) and hydroxybenzotriazole hydrate (HOBt), and a base, such as diisopropylethylamine (DIEA) or triethylamine, in an aprotic solvent, such as methylene chloride. Suitable solvents include methylene chloride and dimethyl formamide, preferably methylene chloride. The aforesaid reaction may be run at a temperature from about 0° C. to about 50° C., for a period from about 1 hour to about 16 hours (as illustrated in *Comprehensive Organic Transformation*, R. C. Larock, VCH Publisher, Inc. (1989) pp. 972–976).

Compounds of the formulae VIII, IX, X and XI are commercially available or can be made by methods well known to those of ordinary skill in the art.

Scheme 3 refers to the preparation of the compounds of formula V which are intermediates useful in the preparation of compound of formula I, in Scheme 1. Referring to Scheme 3, a compound of formula V is prepared by reduction of a compound of the formula XII. Reduction may be effected with hydrogen gas (H$_2$), using catalysts such as palladium on carbon (Pd/C), palladium on barium sulfate (Pd/BaSO$_4$), platinum on carbon (Pt/C), or tris(triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis*, Paul Rylander, Academic Press Inc., San Diego, 31–63 (1979). The following conditions are preferred: Pd on carbon, methanol at 25° C. and 50 psi of hydrogen gas pressure.

An alternative procedure employing the use of reagents such as ammonium formate and Pd/C in methanol at the reflux temperature under an inert atmosphere (e.g., nitrogen or argon gas) is also effective.

Another alternative reduction procedure, for use when R$^1$ contains a group incompatible with the above hydrogenation conditions (e.g., an olefin or halide group), is a dissolving metal reduction wherein the compound of formula XII is treated with a metal, such as zinc, tin or iron, in the presence of an acid such as hydrochloric or sulfuric acid. The aforesaid reaction may be run at a temperature from about 0° C. to about 100° C., for a period from about 1 hour to about 16 hours.

Compounds of the formula XII can be prepared from compounds of formula XIII by reaction with reagents of the formulae VIII, IX and X as described previously in Scheme 2 for the conversion of a compound of formula VII to II.

The starting materials of the formula XIII are either commercially available or known in the art.

Scheme 4 refers to alternate preparations of compounds of formula I.

Referring to Scheme 4, compounds of the formula I, wherein R$^1$ is a nitrogen linked (C$_1$–C$_{10}$)heterocyclyl, can be prepared by an aryl palladium coupling reaction. Aryl palladium coupling reactions are well known to those skilled in the art. One well known coupling method, so called Buchwald and Hartwig conditions, involves the coupling of a compound of formula XIV, wherein L$^2$ is Cl, Br, I or triflate (TfO), with a compound of the formula R$^1$—H, wherein H is a hydrogen on a nitrogen ring atom, in the presence of a palladium (0) catalyst and a base. Palladium (0) catalysts include tris(dibenzylidene acetone)dipalladium(O) (Pd$_2$(dba)$_3$), di(dibenzylidene acetone) palladium(O) (Pd(dba)$_2$), palladium acetate (Pd(OAc)$_2$), and a suitable ligand, such as a triaryl phosphine ligand, tri(t-butyl)phosphine, 1,1'-bis (diphenylphosphanyl)ferrocene (DPPF), 2,2'-bis(diphenylphosphanyl)-1,1'-binaphthyl (BINAP), or PHANEPHOS, preferably tri(ortho-tolyl)phosphine. Suitable bases include K$_2$CO$_3$, K$_2$PO$_4$, CsCO$_3$, LiN(TMS)$_2$ or an alkoxide base such as sodium methoxide, sodium ethoxide, potassium t-butoxide, preferably sodium tert-butoxide. Suitable solvents include toluene or an ethereal solvent, preferably dioxane. The aforesaid reaction may be run at a temperature of about 40° C. to 110° C. for about 1 to 48 hours. Such conditions are reviewed in *Angew. Chem. Int. Ed. Engl.* 1998, 37, 2046–2067 and are well known to those of ordinary skill in the art. Preferred Buchwald conditions use palladium acetate (Pd(OAc)$_2$) or palladium tetra-triphenylphosphine (Pd(PPh$_3$)$_4$) as the source of the palladium. Suitable solvents include THF, toluene or ethereal solvents. The aforesaid reaction may be run at a temperature of about 25° C. to 110° C. for about 1 to 4 hours, preferably 2 hours. Nickel catalysts, such as Ni(cod) (nickel 1,5-cyclooctadiene), are also well known.

Alternatively, compounds of formula I, can be prepared according to a so called Ullmann reaction by reaction of a compound of the formula XIV, wherein L$^2$ is a halide, with a compound of the formula R$^1$—H, wherein H is a hydrogen on a nitrogen ring atom, in the presence of a suitable base and a suitable catalyst. Suitable bases include alkali metal carbonates or hydroxide bases, preferably potassium carbonate. Suitable catalysts include copper (0) catalyst, preferably finely powdered copper bronze. Suitable solvents for the aforesaid reaction include neat or polar aprotic solvents, such as dimethylformamide (DMF), N,N dimethylacetamide or N-methylpyrrolidinone (NMP). The aforesaid reaction may be run at a temperature between about 80° C. and 180° C. for about 6 to 24 hours.

Alternatively, coupling can be carried out by a so called Suzuki coupling reaction of said compound of formula XIV, wherein L$^2$ is borate or boronic acid, with an R$^1$—H, wherein H is a hydrogen on a nitrogen ring atom, a catalyst, a base and a dehydrating agent. Suitable borates include (HO)$_2$B—, 9-BBN, and alkylboranes. Suitable catalysts include copper or palladium (such as palladium acetate (Pd(OAc)$_2$), palladium triphenylphosphine or Pd(dppf)Cl$_2$), preferably copper (II) acetate. Suitable dehydrating agents include 4 angstrom molecular sieves. Suitable bases include tertiary amine bases, such as triethylamine or pyridine, Na$_2$CO$_3$, sodium ethoxide, and K$_3$PO$_4$. Suitable solvents include methylene chloride, dimethyl sulfoxide (DMSO) or tetrahydrofuran (THF). The aforesaid reaction is typically performed under an atmosphere of oxygen gas at a temperature of about 10° C. to 50° C., preferably about 23° C. for about 6 to 72 hours. Palladium-catalyzed boronic acid couplings are described in Miyaura, N., Yanagi, T., Suzuki, A. *Syn. Comm.* 1981, 11, 7, p. 513.

Alternatively, compounds of formula I can also be prepared from compounds of formula XV or XVI via intermediates of the formula II and XII. The intermediates of the formula II and XII can be converted to compounds of formula I according to the methods of Schemes 1 and 3 respectively. The compounds of formulae II and XII can be prepared from compounds of the formulae XV and XVI, respectively, by coupling reactions analogous to those described above for the conversion of compounds of formula XIV to formula I.

Compounds of formula XIV can be prepared from compounds of formula XV or XVI by methods analogous to the conversion of compounds of formula II to I and XII to I.

Compounds of the formula XV and XVI are commercially available or can be made by methods well known to those skilled in the art.

Scheme 5 refers to an alternate preparation of compounds of formula I. Referring to Scheme 5, a compound of formula I is prepared from a compound of formula XVII by reduction with tin in the presence of an acid such as hydrochloric acid followed by a so called Sandmeyer reaction wherein a diazonium intermediate is prepared by treatment with sodium nitrite followed by cuprous halide quench such as cuprous chloride or cuprous bromide. Suitable solvents include alcohols such as methanol and ethanol. The aforesaid reaction is conducted at a temperature from about −20° C. to about 0° C., and the reaction is generally run for a period of about 1 to 48 hours.

The compound of formula XVII, wherein $R^1$ is a standard transformable group, such a —$NH_2$, or a heterocycle can be prepared from a compound of the formula XVIII by reaction with a nucleophile according to standard chemical methods well known to those skilled in the art. Methods for nucleophilic aromatic substitution are reviewed in Belfield et al., *Tetrahedron*, 55, 11399–11428 (1999) and in March, *Advanced Organic Chemistry*, 641–676 (John Wiley & Sons, Inc., Fourth Edition, 1992).

Other compounds of formula XVII, wherein $R^1$ is a nitrogen linked $(C_1-C_{10})$heterocyclyl containing one to six heteroatoms independently selected from —N=, —N<, —NH—, —O— and —S(O)$_n$—; wherein said nitrogen linked $(C_1-C_{10})$heterocyclyl is substituted by at least one oxo substituent; wherein said nitrogen linked $(C_1-C_{10})$ heterocyclyl may also optionally be substituted on any carbon atom able to support an additional substituent, by one to three $R^9$ substituents per ring, each $R^9$ is independently selected from the group consisting of hydrogen, halo, hydroxy, amino, —CN, $(C_1-C_4)$alkyl, $(C_1-C_4)$alkoxy, $HO_2C$—, $R^4R^5N(O_2S)$—, $(C_1-C_4)$alkyl-$(O_2S)$—NH—, $(C_1-C_4)$alkyl-$O_2S$—[$(C_1-C_4)$alkyl-N]—, $R^4R^5N(O=C)$—, $(C_1-C_4)$alkyl-NH—, [$(C_1-C_4)$alkyl]$_2$-N—, $R^4R^5N$ $(CH_2)_t$—, $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$ cycloalkyl-O—, $(C_1-C_{10})$heteroaryl-O— and $(C_1-C_{10})$heterocyclyl-O—; wherein said $(C_1-C_{10})$heterocyclyl may also optionally be substituted on any ring nitrogen atom able to support an additional substituent by one to two $R^{10}$ substituents per ring, each $R^{10}$ is independently selected from the group consisting of hydrogen, $(C_1-C_4)$alkyl, $(C_1-C_4)$alkyl-(C=O)—, $(C_6-C_{10})$aryl, $(C_3-C_8)$cycloalkyl, $(C_1-C_{10})$heteroaryl and $(C_1-C_{10})$heterocyclyl; wherein each of the aforesaid $(C_6-C_{10})$aryl, $(C_3-C_8)$cycloalkyl, $(C_1-C_{10})$heteroaryl and $(C_1-C_{10})$heterocyclyl anywhere on said $R^9$ and $R^{10}$ group members or substituents may optionally be substituted by one to three moieties per ring, independently selected from the group consisting of halo, hydroxy, amino, —CN, $(C_1-C_4)$alkyl, $(C_1-C_4)$alkoxy, —$CF_3$, $CF_3O$—, $(C_1-C_4)$alkyl-NH—, [$(C_1-C_4)$alkyl]$_2$-N—, $(C_1-C_4)$alkyl-S—, $(C_1-C_4)$alkyl-(S=O)—, $(C_1-C_4)$alkyl-$(SO_2)$—, —$(C_1-C_4)$alkyl-O—(C=O)—, formyl, and $(C_1-C_4)$alkyl-(C=O)—; can be prepared by standard conversion methods from compounds of formula XVII, wherein $R^1$ is a standard transformable group.

Compounds of formula XVIII are commercially available or can be made by methods known to those skilled in the art.

Alternatively, compounds of formula I and II can be prepared from compounds of formula XX by analogous Sandmeyer methods as described above.

Compounds of formula XX can be prepared from compounds of formula XXI by methods analogous to the conversion of compounds of formula XVIII to XVII described above.

Compounds of formula XXI are commercially available or can be made by methods well known to those skilled in the art.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^4$ includes a 6-azauracil or barbituric acid moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The activity of the compounds of the invention for the various disorders described above can be determined according to one or more of the following assays. All of the compounds of the invention, that were tested, had an $IC_{50}$ of less than 1 µM in the in vitro assay described below.

Pharmacological Analysis

Certain compounds such as benzoylbenzoyl adenosine triphosphate (bbATP) are known to be agonists of the $P2X_7$ receptor, effecting the formation of pores in the plasma membrane (Drug Development Research (1996), 37(3), p. 126). Consequently, when the receptor is activated using bbATP in the presence of ethidium bromide (a fluorescent DNA probe), an increase in the fluorescence of intracellular DNA-bound ethidium bromide is observed. Alternatively, the propidium dye YOPRO-1 can be substituted for ethidium bromide so as to detect uptake of the dye. The increase in fluorescence can be used as a measure of $P2X_7$ receptor activation and therefore to quantify the effect of a compound on the $P2X_7$ receptor.

In this manner, the compounds of the invention can be tested for antagonist activity at the $P2X_7$ receptor. 96-Well flat bottomed microtitre plates are filled with 250 µl of test solution comprising 200 µl of a suspension of THP-1 cells ($2.5 \times 10^6$ cells/ml, more preferably prestimulated as described in the literature with a combination of LPS and TNF to promote receptor expression) containing $10^{-4}$M ethidium bromide, 25 µl of a high potassium, Low Sodium Buffer Solution (10 mM Hepes, 150 mM KCl, 5 mM D-glucose and 1.0% FBS at pH 7.5) containing $10^{-5}$M bbATM, and 25 µl of the high potassium buffer solution containing $3 \times 10^{-5}$M test compound (more preferably $5 \times 10^{-4}$M, more preferably $1 \times 10^{-4}$M, more preferably $1 \times 10^{-3}$M). The plate is covered with a plastic sheet and incubated at 37° C. for one hour. The plate is then read in a Perkin-Elmer fluorescent plate reader, excitation 520 nm, emission 595 nm, slit widths: Ex 15 nm, Em 20 nm. For the purposes of comparison, bbATP (a $P2X_7$ receptor agonist) and pyridoxal 5-phosphate (a $P2X_7$ receptor antagonist) can be used separately in the test as controls. From the readings obtained, a $pIC_{50}$ figure can be calculated for each test compound, this figure being the negative logarithm of the concentration of test compound necessary to reduce the bbATP agonist activity by 50%.

In like manner, the compounds of the invention can be tested for antagonist activity at the $P2X_7$ receptor using the cytokine IL-1 β as the readout. Blood collected from normal volunteers in the presence of heparin is fractionated using lymphocyte separation medium obtained from Organon Technica (Westchester, Pa.). The region of the resulting gradient containing banded mononuclear cells is harvested, diluted with 10 ml of Maintenance Medium (RPMI 1640, 5% FBS, 25 mM Hepes, pH 7.2, 1% penicillin/streptomycin), and cells are collected by centrifugation. The resulting cell pellet was suspended in 10 ml of Maintenance Medium and a cell count was performed. In an average experiment, $2 \times 10^5$ mononuclear cells are seeded into each well of 96-well plates in a total volume of 0.1 ml. Monocytes are allowed to adhere for 2 hours, after which the supernatants are discarded and the attached cells are rinsed twice and then incubated in Maintenance Medium overnight at 37° C. in a 5% $CO_2$ environment.

The cultured monocytes can be activated with 10 ng/ml LPS (E. coli serotype 055:B5; Sigma Chemicals, St. Louis, Mo.). Following a 2-hour incubation, the activation medium is removed, the cells are rinsed twice with 0.1 ml of Chase Medium (RPMI 1640, 1% FBS, 20 mM Hepes, 5 mM $NaHCO_3$, pH 6.9), and then 0.1 ml of Chase Medium containing a test agent is added and the plate is incubated for 30 minutes; each test agent concentration can be evaluated in triplicate wells. ATP then is introduced (from a 100 mM stock solution, pH 7) to achieve a final concentration of 2 mM and the plate is incubated at 37° C. for an additional 3 hours. Media were harvested and clarified by centrifugation, and their IL-1β content was determined by ELISA (R&D Systems; Minneapolis, Minn.).

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous), topical or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution, dry powder formulation or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, heptafluoroalkanes, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (inflammation) is 0.1 to 200 mg of the active ingredient per unit dose which could be administered, for example, 1 to 4 times per day.

The compound of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Aerosol formulations for treatment of the conditions referred to above in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

Aerosol combination formulations for treatment of the conditions referred to above (e.g., adult respiratory distress syndrome) in the average adult human are preferably arranged so that each metered dose or "puff" of aerosol contains from about 1 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

Aerosol formulations for treatment of the conditions referred to above (e.g., adult respiratory distress syndrome) in the average adult human are preferably arranged so that each metered dose or "puff" of aerosol contains from about 20 µg to 1000 µg of the compound of the invention. The overall daily dose with an aerosol will be within the range 100 µg to 10 mg of the p38 kinase inhibitor. Administration may be several times daily, for example 2, 3, 4 or 8 times, giving for example, 1, 2 or 3 doses each time.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonitrile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 AMU to 1100 AMU. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

One of ordinary skill in the art will appreciate that in some cases protecting groups may be required during preparation. After the target molecule is made, the protecting group can be removed by methods well known to those of ordinary skill in the art, such as described in Greene and Wuts, "Protective Groups in Organic Synthesis" ($2^{nd}$ Ed, John Wiley & Sons 1991).

EXAMPLE 1

2-Chloro-5-(3,5-dioxo-4,5-dihydro-3H-[1,2,4]triazin-2-yl)-N-(2-ethyl-hexyl)-benzamide

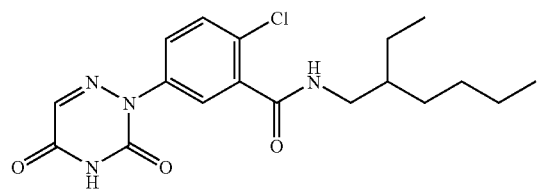

A: 2-(3-Carboxy-4-chloro-phenyl)-3,5-dioxo-2,3,4,5-tetrahydro-[1,2,4]triazine-6-carboxylic acid

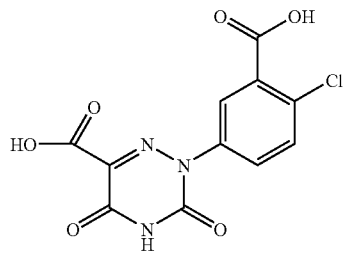

To a mechanically stirred solution of 5-amino-2-chlorobenzoic acid methyl ester (5.0 g, 26.9 mmol) in glacial acetic acid (100 ml) was added 12 N hydrochloric acid (7.5 ml). After 30 minutes at room temperature the reaction mixture was cooled to 10° C. and a solution of NaNO$_2$ in water (5 ml) was added dropwise at a rate that kept the reaction temperature between 10° and 15° C. During this time it was observed that the reaction went from purple to light brown. After stirring for 30 minutes at 10° C. sodium acetate (5.4 g) followed by (3-ethoxycarbonylamino-3-oxo-propionyl)-carbamic acid ethyl ester (7.2 g) were added at once. After stirring for 20 minutes at 10° C. followed by 1 hour at room temperature an additional 2.2 g of sodium acetate was added. After stirring at reflux for 6 hours the reaction mixture was cooled to room temperature and 50% aqueous sulfuric acid (29 ml) was added. After stirring the resulting mixture at reflux for 2 hours the mixture was cooled to room temperature, diluted with water (135 ml) and filtered. The precipitate was washed with water and dried under vacuum. The crude solid was recrystallized from isopropyl ether to give 3.8 g (46%) of the title intermediate as an orange solid. Mass spec [M−1] 3:1 ratio of 310.1 and 312.1; $^1$H nmr (500 MHz, CD$_3$OD) δ 7.64 (d, J=8.8 Hz, 1H), 7.75 (d, J=8.8 Hz, 1H), 8.14 (d, J=2.6 Hz, 1H).

B: 2-Chloro-5-(3,5-dioxo-4,5-dihydro-3H-[1,2,4]triazin-2-yl)-benzoic acid

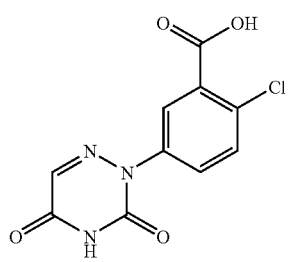

A suspension of 2-(3-carboxy-4-chloro-phenyl)-3,5-dioxo-2,3,4,5-tetrahydro-[1,2,4]triazine-6-carboxylic acid (3.4 g) in mercaptoacetic acid (2 ml) was stirred at 175° C. After 20 h the resulting solution was cooled to room temperature during which time a precipitate formed. The mixture was dumped into ice-water, stirred for 30 minutes and filtered to give a yellow solid. The solid was dried under vacuum for 24 hours to give 2.1 g of the title intermediate. Mass spectrum [M−1] 3:1 ratio of 266.1 and 268.1; $^1$H nmr (500 MHz, CD$_3$OD) δ 7.58 (s, 1H), 7.60 (d, J=8.8 Hz, 1H), 7.72 (dd, J=2.6 and 8.8 Hz), 8.09 (d, J=2.6 Hz).

C: 2-Chloro-5-(3,5-dioxo-4,5-dihydro-3H-[1,2,4]triazin-2-yl)-benzoyl chloride

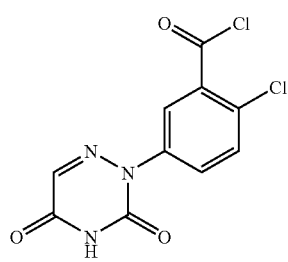

A mixture of 2-chloro-5-(3,5-dioxo-4,5-dihydro-3H-[1,2,4]triazin-2-yl)-benzoic acid (50 mg) in thionyl chloride (1 ml) was stirred at reflux for 1 hour. The mixture was concentrated under vacuum to provide 50 mg of the title intermediate as an amorphous amber solid that was used immediately in the next step.

D: 2-Chloro-5-(3,5-dioxo-4,5-dihydro-3H-[1,2,4]triazin-2-yl)-N-(2-ethyl-hexyl)-benzamide To a solution of 2-ethylhexylamine (15 mg, 0.125 mmol) in dichloroethane (1 ml) was added diisopropylethylamine resin (60 mg, 0.225 mmol) followed by a solution of 2-chloro-5-(3,5-dioxo-4,5-dihydro-3H-[1,2,4]triazin-2-yl)-benzoyl chloride (21 mg, 0.075 mmol) in a 3:1 mixture of dichloroethane and THF (15 ml). The reaction mixture was shaken for 16 hours and filtered. The filtrate was treated with MP-carbonate resin (75 mg, 0.225 mmol) and the resulting mixture was shaken for 3 hours. The mixture was filtered and the resin washed with dichloromethane followed by 9:1 methanol/acetic acid. The combined filtrates were concentrated under reduced pressure to give the title compound as an amorphous solid. Mass spec [M−1] 3:1 ratio of 377.2 and 379.2; $^1$H nmr (500 MHz, CDCl$_3$) δ 0.92 (t, 3H), 0.96 (t, 3H), 1.26–1.66 (m, 9H), 3.46 (m, 2H), 6.26 (broad s, 1H), 7.51 (d, 1H), 7.59–7.62 (m, 2H), 7.94 (s, 1H), 8.72 (broad s, 1H).

Examples 2–44 are presented in Table 1 and were prepared analogously to the synthesis outlined in Example 1D, coupling the appropriate amine to 2-chloro-5-(3,5-dioxo-4,5-dihydro-3H-[1,2,4]triazin-2-yl)-benzoyl chloride. In some examples the product was purified by preparative HPLC using a Shimadsu LC-8A preparative liquid chromatograph. All final products were analyzed by LC/MS using a Micromass ZMD LC/MS (ESI mode). The method used for the HPLC mobile phase gradient change was as follows:

| Time (min) | A % | B % |
| --- | --- | --- |
| 0.00 | 95 | 5 |
| 1.0 | 80 | 20 |
| 2.3 | 50 | 50 |
| 3.7 | 0 | 100 |
| 3.7 | 95 | 5 |

Solvent A = 98% Water + 2% Acetonitrile + 0.01% Formic Acid
Solvent B = Acetonitrile + 0.005% Formic Acid

TABLE 1

| Ex. | Structure | Mass Spectra (ES+) | Mass Spectra (ES−) | LC Retention Time (min) |
|---|---|---|---|---|
| 2 | 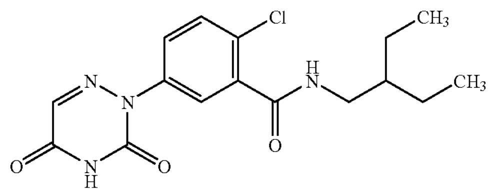 | 351.2 | 349.2 | 2.2 |
| 3 | 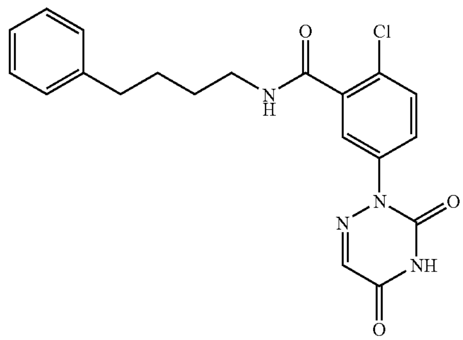 | 399.1 | 397.0 | 2.4 |
| 4 | 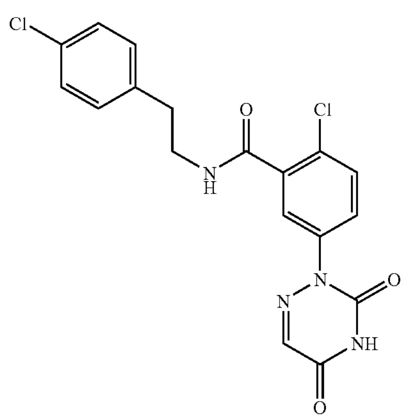 | 405.0 | 403.0 | 2.3 |
| 5 | 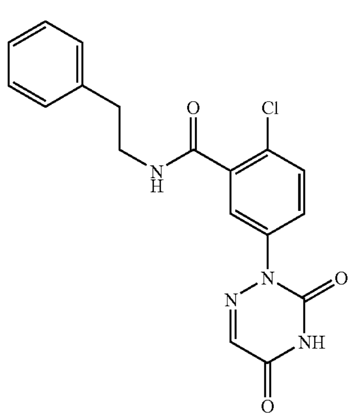 | 371.1 | 369.0 | 2.0 |

TABLE 1-continued

| Ex. | Structure | Mass Spectra (ES+) | Mass Spectra (ES−) | LC Retention Time (min) |
|---|---|---|---|---|
| 6 | 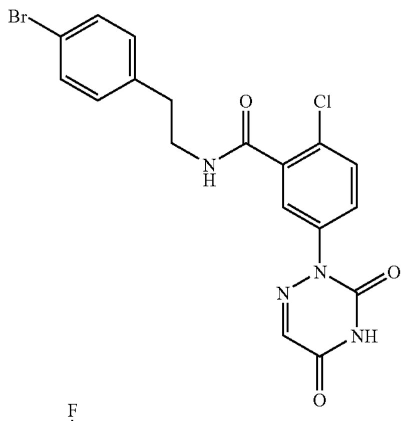 | 451.0 | 448.9 | 2.3 |
| 7 | 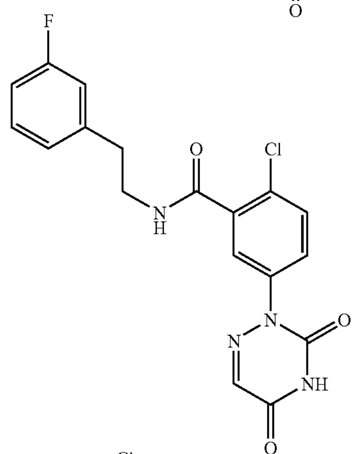 | 389.1 | 387.0 | 2.1 |
| 8 | 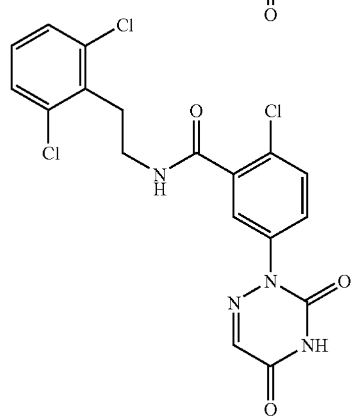 | 441.0 | 436.9 | 2.3 |
| 9 | 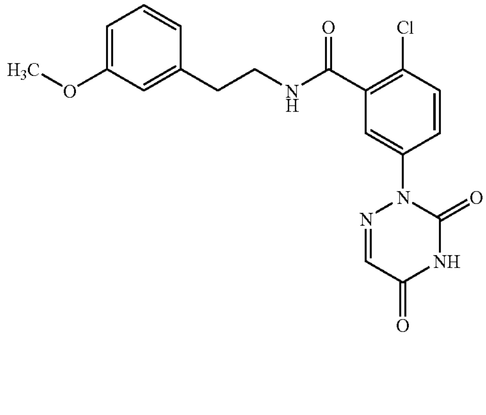 | 401.1 | 399.0 | 2.2 |

TABLE 1-continued

| Ex. | Structure | Mass Spectra (ES+) | Mass Spectra (ES−) | LC Retention Time (min) |
| --- | --- | --- | --- | --- |
| 10 | 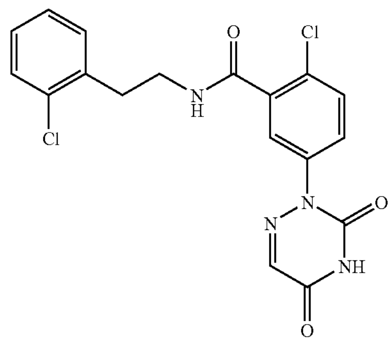 | 405.0 | 403.0 | 2.2 |
| 11 | 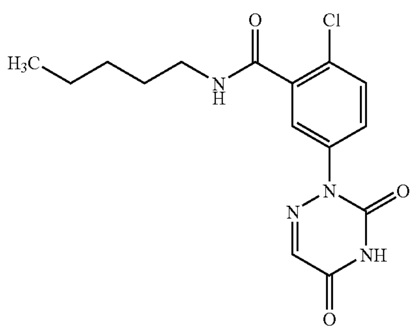 | 337.1 | 335.1 | 2.1 |
| 12 | 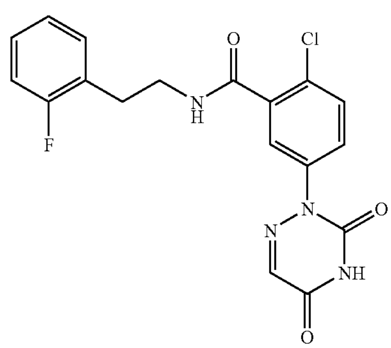 | 389.1 | 387.0 | 2.0 |
| 13 | 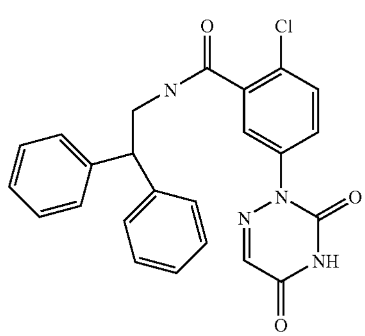 | 447.1 | 445.0 | 2.4 |

TABLE 1-continued

| Ex. | Structure | Mass Spectra (ES+) | Mass Spectra (ES−) | LC Retention Time (min) |
|---|---|---|---|---|
| 14 | 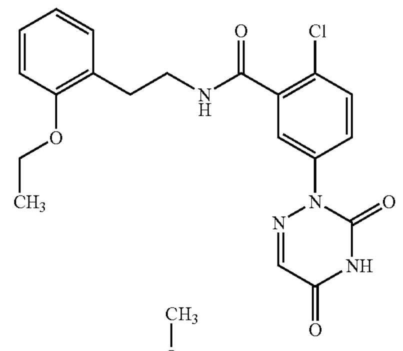 | 415.1 | 413.0 | 2.3 |
| 15 | 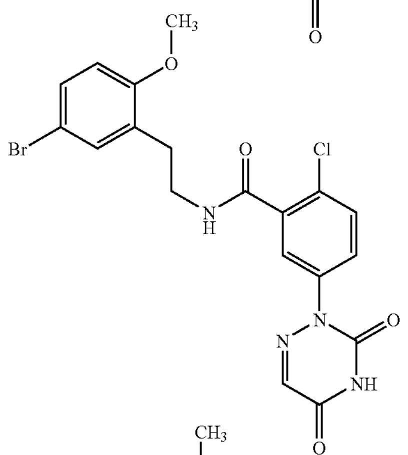 | 481.0 | 479.0 | 2.3 |
| 16 | 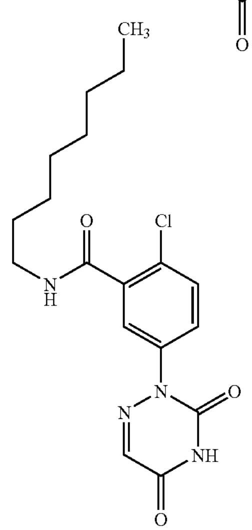 | 379.2 | 377.1 | 2.7 |
| 17 | 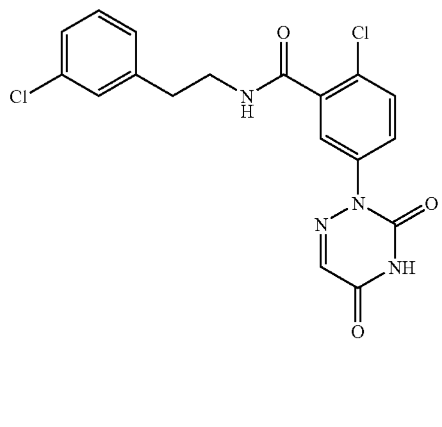 | 405.0 | 403.0 | 2.2 |

TABLE 1-continued
| Ex. | Structure | Mass Spectra (ES+) | Mass Spectra (ES−) | LC Retention Time (min) |
|---|---|---|---|---|
| 18 | 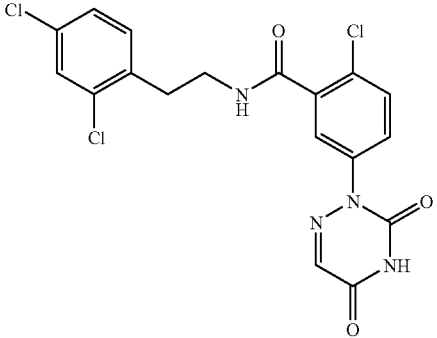 | 439.0 | 438.9 | 2.5 |
| 19 | 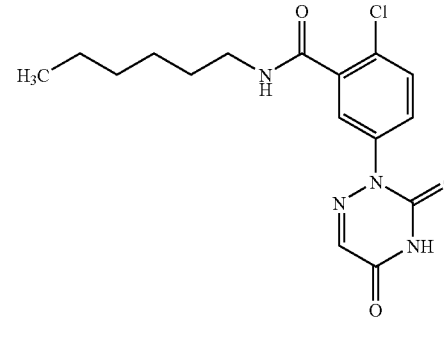 | 351.2 | 349.1 | 2.3 |
| 20 | 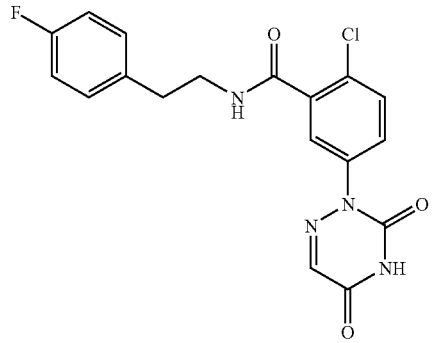 | 389.1 | 387.0 | 2.1 |
| 21 | 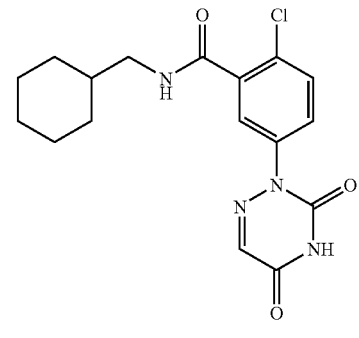 | 363.2 | 361.1 | 2.2 |

TABLE 1-continued

| Ex. | Structure | Mass Spectra (ES+) | Mass Spectra (ES−) | LC Retention Time (min) |
| --- | --- | --- | --- | --- |
| 22 | 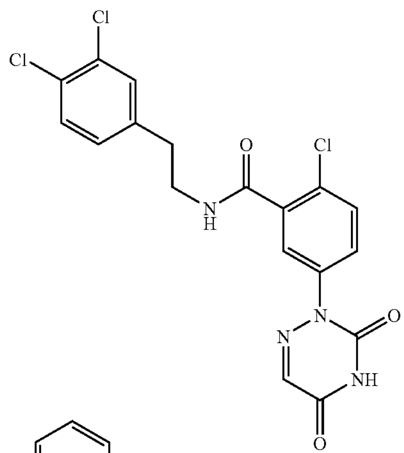 | 441.0 | 439.0 | 2.4 |
| 23 | 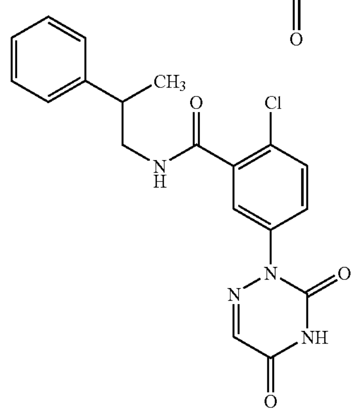 | 385.1 | 383.0 | 2.3 |
| 24 | 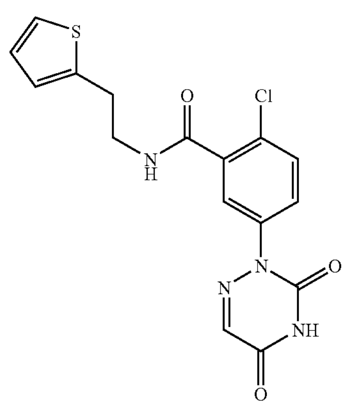 | 377.1 | 375.0 | 1.9 |
| 25 | 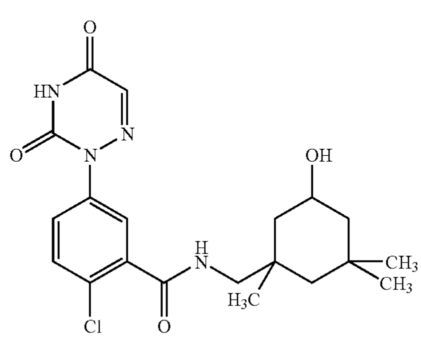 | 421.7 | 419.8 | 2.0 |

TABLE 1-continued

| Ex. | Structure | Mass Spectra (ES+) | Mass Spectra (ES−) | LC Retention Time (min) |
|---|---|---|---|---|
| 26 | 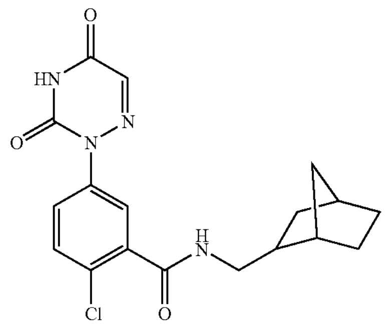 | 375.6 | 373.7 | 2.4 |
| 27 | 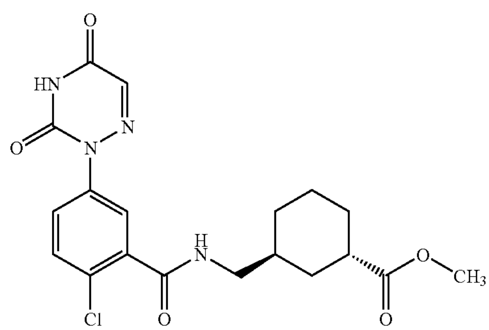 | 421.9 | 419.6 | 2.1 |
| 28 | 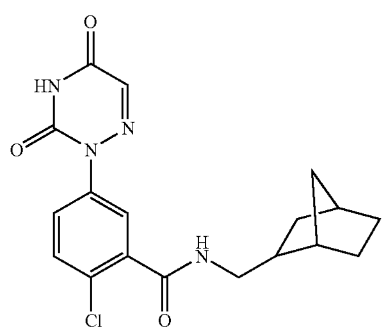 | 375.8 | 373.8 | 2.4 |
| 29 | 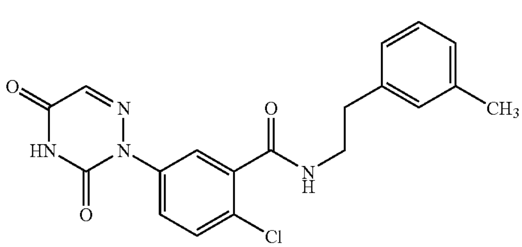 | 385.2 | 383.1 | 2.2 |

TABLE 1-continued

| Ex. | Structure | Mass Spectra (ES+) | Mass Spectra (ES−) | LC Retention Time (min) |
|---|---|---|---|---|
| 30 | 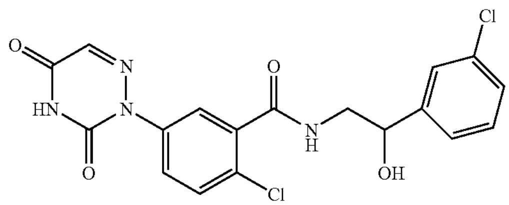 | 421.1 | 419.1 | 1.9 |
| 31 | 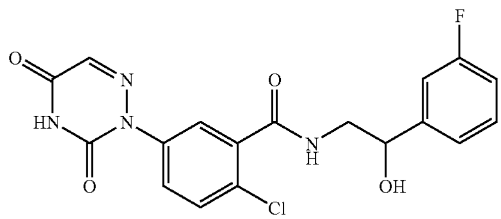 | 405.2 | 403.1 | 1.7 |
| 32 | 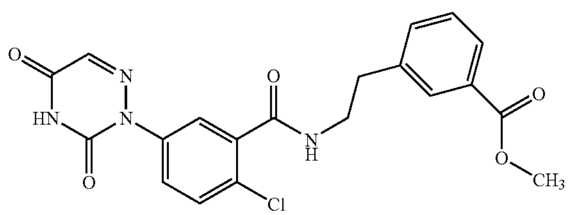 | 429.2 | 427.1 | 2.0 |
| 33 | 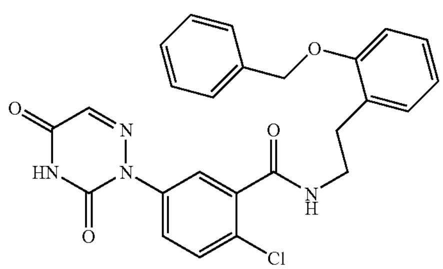 | 477.2 | 475.2 | 2.6 |
| 34 | Chiral | 403.3 | 401.2 | 2.6 |
| 35 | 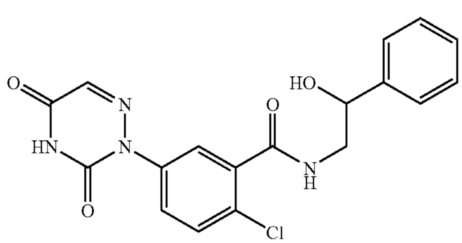 | 387.2 | 385.1 | 1.5 |

TABLE 1-continued

| Ex. | Structure | Mass Spectra (ES+) | Mass Spectra (ES−) | LC Retention Time (min) |
| --- | --- | --- | --- | --- |
| 36 | 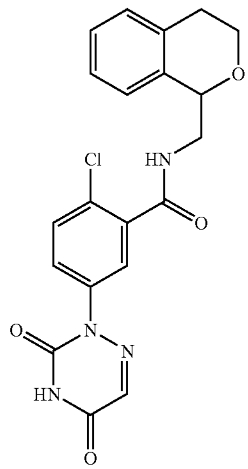 | 413.2 | 411.1 | 2.0 |
| 37 | 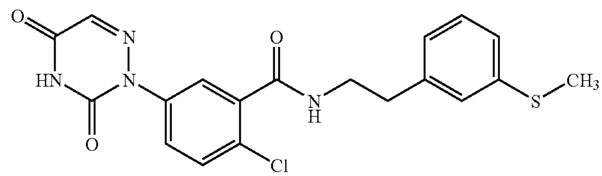 | 417.2 | 415.1 | 2.2 |
| 38 | 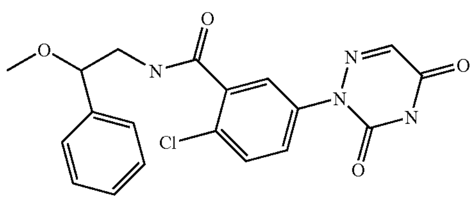 | 401.2 | 399.1 | 2.0 |
| 39 | 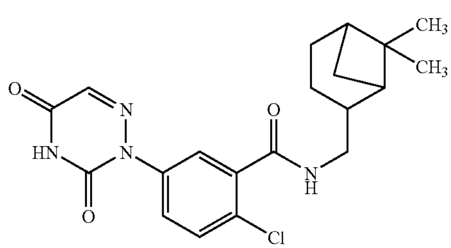 | 403.3 | 401.2 | 2.6 |
| 40 | 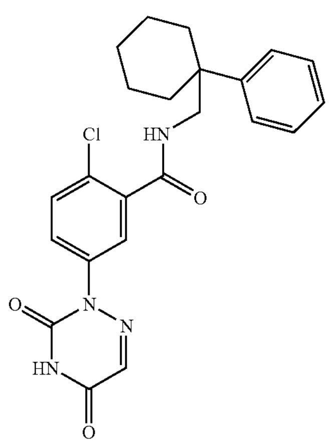 | 439.3 | 437.2 | 2.6 |

TABLE 1-continued
| Ex. | Structure | Mass Spectra (ES+) | Mass Spectra (ES−) | LC Retention Time (min) |
|---|---|---|---|---|
| 41 | 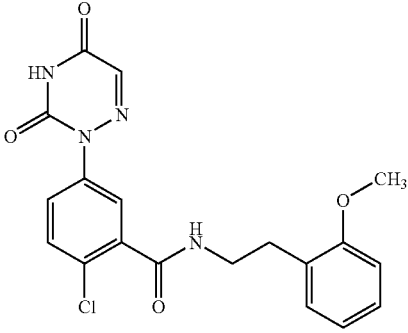 | 401.5 | 399.6 | 2.1 |
| 42 | 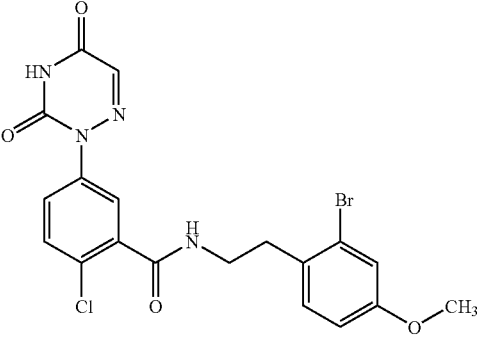 | 481.5 | 479.5 | 2.2 |
| 43 | 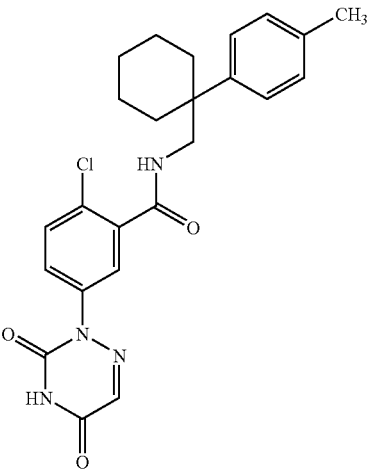 | 453.3 | 451.2 | 2.8 |
| 44 | 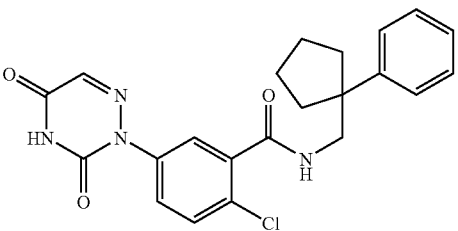 | 425.3 | 423.2 | 2.5 |

TABLE 1-continued

| Ex. | Structure | Mass Spectra (ES+) | Mass Spectra (ES−) | LC Retention Time (min) |
| --- | --- | --- | --- | --- |
| 45 | 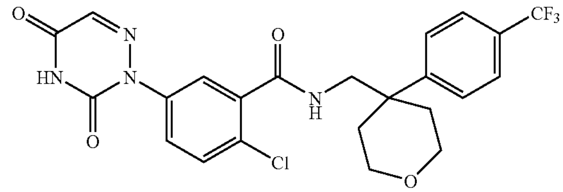 | 510.1 | 508.1 | 2.4 |
| 46 | 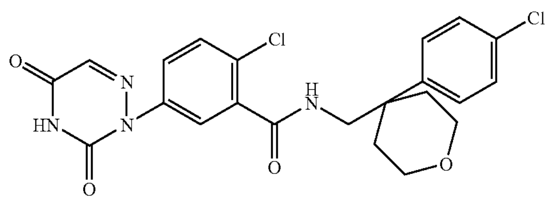 | 475.2 | 473.2 | 2.2 |
| 47 | 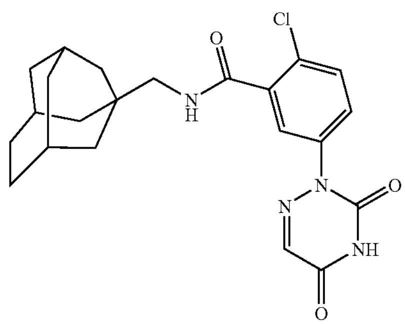 | 429.5 | 427.5 | 2.7 |

EXAMPLE 48

2-Chloro-5-(3,5-dioxo-4,5-dihydro-3H-[1,2,4]triazin-2-yl)-N-[2-(2-trifluoromethyl-phenyl)-ethyl]-benzamide

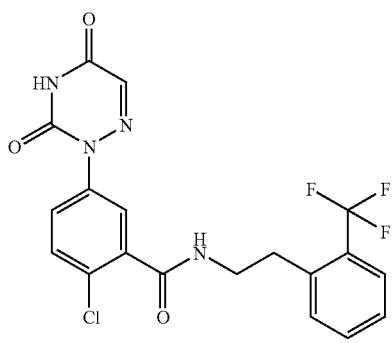

To a stirred solution of 2-chloro-5-(3,5-dihydro-3H-[1,2,4]triazin-2-yl)-benzoic acid (75 mg, 0.3 mmol), EDCI (60 mg) and HOBT (50 mg) in DMF (3 ml) was added 2-(2-trifluoromethylphenyl)ethylamine (53 mg, 0.3 mmol). After 30 minutes triethylamine (45 µl) was added. After 3 hours the reaction mixture was diluted with ethyl acetate (75 ml) and washed sequentially with water and brine. The organic layer was dried over magnesium sulfate, filtered and concentrated under vacuum to give 73 mg of an amorphous solid. The solid was purified by silica gel chromatography eluting with 1:1 ethylacetate/hexanes, followed by crystallization from isopropyl ether to give 36 mg of the title compound as a white solid.

Melting Point=148–150° C.; Mass spectra [M−1] 437.6; Mass spectra [M+1] 439.9.

Examples 49–50 are presented in Table 2 and were prepared analogously to the synthesis outlined in Example 48, coupling the appropriate amine to 2-chloro-5-(3,5-dioxo-4,5-dihydro-3H-[1,2,4]triazin-2-yl)-benzoic acid. Final products were analyzed by LC/MS using a Micromass ZMD LC/MS (ESI mode). The method used for the HPLC mobile phase gradient change was as follows:

| Time (min) | A % | B % |
| --- | --- | --- |
| 0.00 | 95 | 5 |
| 1.0 | 80 | 20 |
| 2.3 | 50 | 50 |
| 3.7 | 0 | 100 |
| 3.7 | 95 | 5 |

Solvent A = 98% Water + 2% Acetonitrile + 0.01% Formic Acid
Solvent B = Acetonitrile + 0.005% Formic Acid

TABLE 2

| Ex. | Structure | Mass Spectra (ES+) | Mass Spectra (ES−) | LC Retention Time (min) |
|---|---|---|---|---|
| 49 | 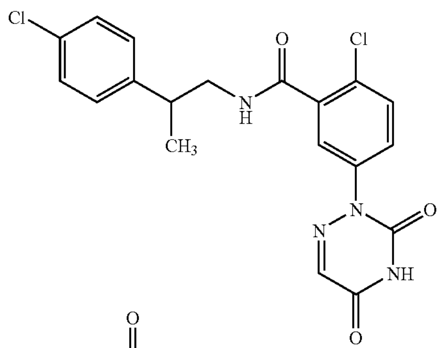 | 419.5 | 417.5 | 2.4 |
| 50 | 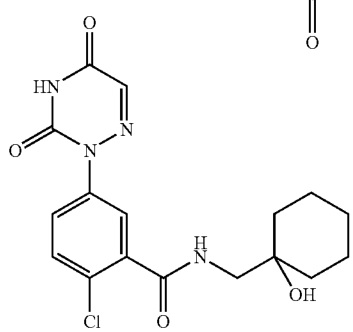 | 379.4 | 377.4 | 1.6 |

EXAMPLE 51

N-[2-(2-Chloro-phenyl)-ethyl]-5-(3,5-dioxo-4,5-dihydro-3H-[1,2,4]triazin-2-yl)-2-methyl-benzamide

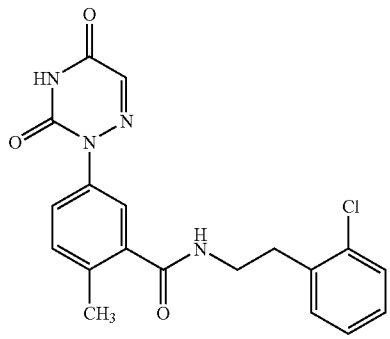

A: 2-Methyl-5-(3,5-dioxo-4,5-dihydro-3H-[1,2,4]triazin-2-yl)-benzoic acid

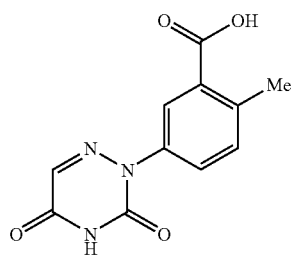

5-Amino-2-chloro-benzoic acid methyl ester (3.5 g, 21.2 mmol) was dissolved in glacial acetic acid (80 ml) and 5.5 ml of concentrated HCl was added. After stirring with an overhead stirrer for 30 minutes at ambient temperature the mixture was cooled to 10° C. and a solution of NaNO$_2$ (1.6 g) in water (4 ml) was added dropwise, keeping the internal temperature below 15° C. During this addition the reaction mixture changed from amber to a cloudy orange. After 30 minutes sodium acetate (3.8 g, 46.6 mmol) and (3-ethoxycarbonylamino-3-oxo-propionyl)-carbamic acid ethyl ester (5.7 g, 23.3 mmol) were added at once. After 10 minutes the reaction was warmed to ambient temperature. After 1 hour additional sodium acetate (1.7 g, 21.2 mmol) was added and the reaction mixture was heated at reflux. After 3 hours the deep red-brown mixture was treated with 50% sulfuric acid (23 ml) and heated again at reflux. After 2 hours the mixture was concentrated under reduced pressure and then water (200 ml) was added. After stirring for 30 minutes the gold precipitate (3.5 g) was collected by filtration. The resulting solid was suspended in 3 ml of mercaptoacetic acid and stirred at 175° C. After 4 hours the mixture was allowed to cool and sit for 16 hours. The mixture was diluted with water (100 ml) and stirred for 1 hour. The resulting brown solid (2.1 g) was collected by filtration. Mass spectrum [M−1] 246.4.

B: N-[2-(2-Chloro-phenyl)-ethyl]-5-(3,5-dioxo-4,-dihyro-3H-[1,2,4]triazin-2-yl)-2-methyl-benzamide The title compound was prepared using the method outlined in Example 48, coupling 2-methyl-5-(3,5-dioxo-4,5-dihydro-3H-[1,2,4]triazin-2-yl)-benzoic acid with 2-(ortho-chlorophenyl)ethylamine. The product was a colorless oil. MS (ES+) 385.2; (ES−) 383.2; LC retention time=2.1 min (using the LC/MS and method outlined for the examples in Table 1).

EXAMPLE 52

2-Chloro-N-[2-(2-chloro-phenyl)-ethyl]-5-(4-methyl-3,5-dioxo-4,5-dihydro-3H-[1,2,4]triazin-2-yl)-benzamide

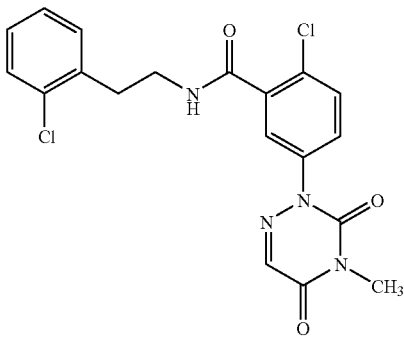

To a stirred solution of 2-chloro-N-[2-(2-chloro-phenyl)-ethyl]-5-(3,5-dioxo-4,5-dihydro-3H-[1,2,4]triazin-2-yl)-benzamide (70 mg, 0.173 mmol) in dioxane (1.5 ml) was added methanol (0.36 ml) followed by a 2.0 M solution of (trimethylsilyl)diazomethane (0.35 ml). After stirring for 16 hours at ambient temperature the mixture was concentrated under reduced pressure to give 75 mg of a white amorphous solid. Purification by silica gel chromatography eluting with 2:1 hexaned/ethyl acetate provided 39 mg of the title compound as a white amorphous solid. Melting Point 157–161° C.;

Mass Spectrum (ES+) 419.2; (ES−) 417.1; LC retention time=2.4 minutes (using the LC/MS and method outlined for the examples in Table 1).

EXAMPLE 53

2-Chloro-N-[2-(2-chloro-phenyl)-ethyl]-5-(2-oxo-piperidin-1-yl)-benzamide

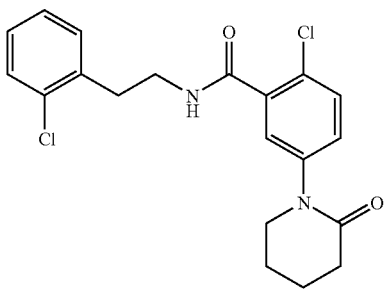

A: 5-Bromo-2-chloro-N-[2-(2-chloro-phenyl)-ethyl]-benzamide

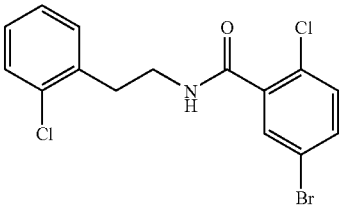

To a stirred solution of 2-chloro-5-bromobenzoic acid (1.5 g, 6.3 mmol), EDCI (1.63 g, 8.5 mmol), and HOBT (1.15 g, 8.5 mmol) in DMF (20 ml) was added 2-(2-chlorophenyl)ethylamine (1.06 ml, 7.5 mmol). After 15 minutes triethylamine (1.18 ml, 8.5 mmol) and DMF (5 ml) was added. After 2 hours at ambient temperature the mixture was diluted with ethyl acetate (50 ml) and washed with 1 N HCl followed by a saturated solution of sodium bicarbonate, followed by water, and then brine. The organic layer was separated and dried over magnesium sulfate, filtered and concentrated under reduced pressure to give 2.12 g of an amorphous solid. Mass Spectrum (ES+) 374.6, (ES−) 372.2.

B: 2-Chloro-N-[2-(2-chloro-phenyl)-ethyl]-5-(2-oxo-piperidin-1-yl)-benzamide

A mixture of 5-bromo-2-chloro-N-[2-(2-chloro-phenyl)-ethyl]-benzamide (200 mg, 0.536 mmol), δ-valerolactam (106 mg, 1.07 mmol), potassium carbonate (156 mg, 1.13 mmol), dioxane (1 ml, purged with nitrogen), and copper (I) iodide (5 mg) in an oven-dried round bottom flask equipped with a reflux condenser under a nitrogen atmosphere was heated in an oil bath at 120–125° C. After 21 hours the mixture was cooled to room temperature, filtered through a pad of silica gel and concentrated under reduced pressure to give 50 mg of crude product. Purification by preparative HPLC (Shimadsu LC-8A preparative liquid chromatograph) eluting with a gradient of 0.1% aqueous formic acid in acetonitrile provided 2.5 mg of the title compound as a colorless amorphous solid. Mass Spectrum (ES+) 391.6; LC retention time=2.3 minutes (using the LC/MS and method outlined for the examples in Table 1).

Examples 54–57 are presented in Table 3 and were prepared analogously to the synthesis outlined in Example 53, coupling the appropriate lactam to 5-bromo-2-chloro-N-[2-(2-chloro-phenyl)-ethyl]-benzamide. In some examples the product was purified by preparative HPLC using a Shimadsu LC-8A preparative liquid chromatograph. All final products were analyzed by LC/MS using a Micromass ZMD LC/MS (ESI mode). The method used for the HPLC mobile phase gradient change was as follows:

| Time (min) | A % | B % |
| --- | --- | --- |
| 0.00 | 95 | 5 |
| 1.0 | 80 | 20 |
| 2.3 | 50 | 50 |
| 3.7 | 0 | 100 |
| 3.7 | 95 | 5 |

Solvent A = 98% Water + 2% Acetonitrile + 0.01% Formic Acid
Solvent B = Acetonitrile + 0.005% Formic Acid TABLE 3
| Ex. | Structure | Mass Spectra (ES+) | Mass Spectra (ES−) | LC Retention Time (min) |
|---|---|---|---|---|
| 54 | 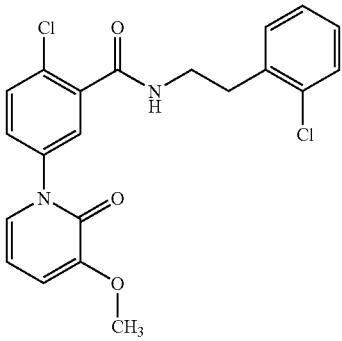 | 417.7 | — | 2.3 |
| 55 | 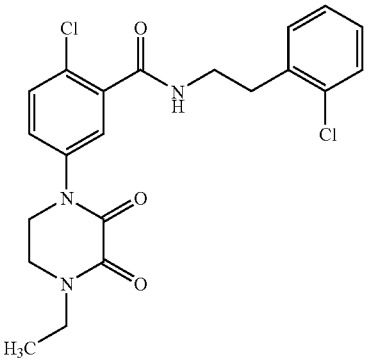 | 434.3 | — | 2.1 |
| 56 | 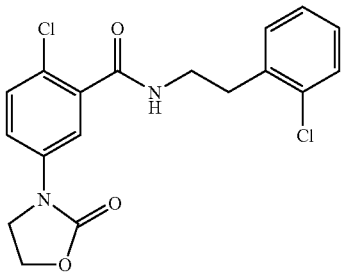 | 379.8 | — | 2.4 |
| 57 | 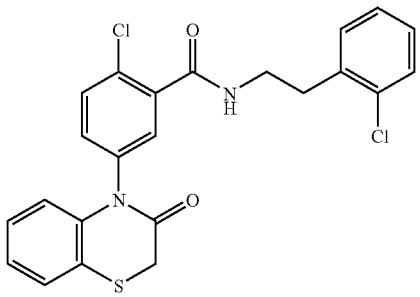 | 457.1 | — | 2.8 |

EXAMPLE 58

2-chloro-N-[2-(2-chloro-phenyl)-ethyl]-5-(5-oxo-1,5-dihydro-[1,2,4]triazol-4-yl)-benzamide

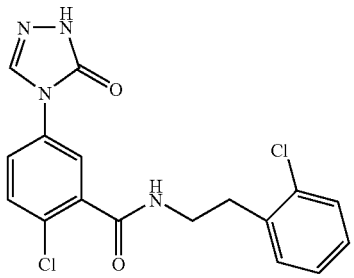

A: 2-Chloro-5-phenoxycarbonylamino-benzoic acid methyl ester

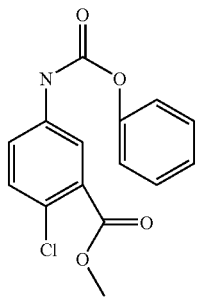

To a stirred mixture of 5-amino-2-chloro-benzoic acid methyl ester hydrochloride (1.110 g, 5.0 mmol) and pyridine (0.79 g, 10.0 mmol) in anhydrous THF (15 mL) at 0° C. was added phenylchloroformate (0.95 g, 6.0 mmol). After warming to room temperature, the reaction mixture was diluted with ethylacetate (50 mL), washed sequentially with 10% HCl, water and brine and dried over sodium sulfate. Removal of solvent under vacuum and purification of the product by flash chromatography (10% ethyl acetate in hexanes) yielded 0.8 g (53%) of a colorless solid. $^1$H NMR (300 MHz, DMSO-d6) δ3.9 (s, 3H), 7.0 (br s, 1H), 7.18 (m, 2H), 7.4 (m, 3H), 7.6 (m, 1H), 7.9 (d, J=2.5 Hz, 1H). Mass Spectrum (M–H): 3:1 ratio of 304 and 306.

B: 1-Formyl-4-(2-Chloro-5-carbomethoxyphenyl) semicarbazide

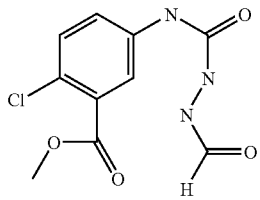

To a solution of 2-chloro-5-phenoxycarbonylamino-benzoic acid methyl ester (0.22 g, 0.72 mmol) in dimethyl sulfoxide (1.4 mL) was added formic hydrazide (0.135 g, 3.15 mmol). After stirring at room temperature for 20 hours, the reaction mixture was partitioned between ethyl acetate and 1.0 N HCl. The organic phase was washed with brine, dried and concentrated in vacuo. The residue was purified on silica gel (30% methanol in ethyl acetate) to yield 0.03 g (17%) of a colorless solid: Mass Spectrum: (M+H) 3:1 ratio of 272 and 274.

C: 2-Chloro-5-(5-oxo-1,5-dihydro-[1,2,4]triazol-4-yl)-benzoic acid

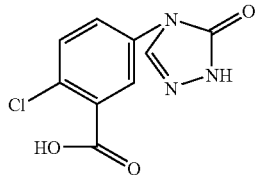

A solution of 1-formyl-4-(2-chloro-5-carbomethoxyphenyl)semicarbazide (0.03 g, 0.11 mmol) in 1.0 M KOH in methanol (MeOH) (0.44 mL) was heated at 80° C. for 72 hours and cooled to room temperature. 1.0 N HCl (0.8 mL) was added and the mixture evaporated to dryness in vacuo. The residue was taken up in MeOH (1.5 mL) and filtered. The filtrate was concentrated in vacuo to yield 0.028 g (100%) of the title intermediate as an amorphous solid. Mass Spectrum (M–H): 3:1 ratio of 238 and 240.

D: 2-Chloro-N-[2-(2-chloro-phenyl)-ethyl]-5-(5-oxo-1,5-dihydro-[1,2,4]triazol-4-yl)-benzamide To a solution of 2-chloro-5-(5-oxo-1,5-dihydro-[1,2,4]triazol-4-yl)-benzoic acid (0.028 g, 0.117 mmol) in anhydrous dimethyl formamide (DMF) (4 mL) was added 1-hydroxybenzotriazole (0.018 g, 0.14 mmol). After stirring at room temperature for 10 minutes, 1-ethyl-3-(3-dimethylaminopropyl) carbodiimide hydrochloride (0.025 g, 0.13 mmol) was added. After stirring at room temperature for 30 minutes, 2-chlorophenethylamine (0.018 g, 0.12 mmol) and triethylamine (0.012 g, 0.12 mmol) were added and the mixture stirred at room temperature overnight. The reaction mixture was diluted with EtOAc, washed sequentially with water and brine, and dried over sodium sulfate. Removal of solvent in vacuo followed by purification by reverse phase HPLC yielded 0.042 g (10%) of the title compound as a colorless solid. $^1$H NMR (300 MHz, CDCl$_3$) δ (m, 2H), 3.45 (m, 2H), 7.25 (m, 2H), 7.35 (m, 2H), 7.60 (d, J=7.9 Hz, 1H), 7.76 (s, 1H), 7.78 (s, 1H), 8.43 (s, 1H) and 8.64 (m, 1H). Mass Spectrum (M–H) 3:1 Ratio of 375 and 377.

What is claimed is:
1. A compound of the formula

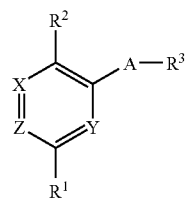

I wherein A is —(C=O)NH— or —NH(C=O)—;
X, Y and Z are =(CR$^6$)—, =(CR$^7$)—, and =(CR$^8$)—;
R$^1$ is a 3-oxo-2,3-dihydro-benzo[1,4]thiazin-4-yl group
n is an integer from zero to two;
q is an integer one or two;
s is an integer from one to three;
R$^2$ is chloro, bromo, (C$_1$–C$_4$)alkyl, —CF$_3$ or —CN;
R$^3$ selected from the group consisting of (C$_4$–C$_{10}$)alkyl, (C$_3$–C$_{12}$)cycloalkyl-(CR$^{11}$R$^{12}$)$_s$—, (C$_6$–C$_{10}$)aryl-(CR$^{11}$R$^{12}$)$_q$—(CH$_2$)—; (C$_1$–C$_{10}$)heterocyclyl-(CR$^{11}$R$^{12}$)$_s$— and (C$_1$–C$_{10}$)heteroaryl-(CR$^{11}$R$^{12}$)$_s$—;
wherein said (C$_4$–C$_{10}$)alkyl may optionally be substituted with one to three substituents independently selected from halo, hydroxy, —CN, $(C_1$–$C_4)$alkyl, $(C_1$–$C_4)$alkoxy, —$CF_3$, $CF_3O$—, $(C_1$–$C_4)$alkyl-S—, $(C_1$–$C_4)$alkyl-(S=O)—, $(C_1$–$C_4)$alkyl-$(SO_2)$—, —$CO_2$—$(C_1$–$C_4)$alkyl, formyl, $(C_1$–$C_4)$alkyl-(C=O)—, $(C_6$–$C_{10})$aryl, $(C_3$–$C_8)$cycloalkyl, $(C_1$–$C_{10})$heteroaryl, $(C_1$–$C_{10})$heterocyclyl, $(C_6$–$C_{10})$aryl-O—, $(C_3$–$C_8)$cycloalkyl-O—, $(C_1$–$C_{10})$heteroaryl-O— and $(C_1$–$C_{10})$heterocyclyl-O—; wherein each of said $R^3$ group members $(C_1$–$C_{10})$heterocyclyl$(CR^{11}R^{12})_s$— and $(C_1$–$C_{10})$heteroaryl$(CR^{11}R^{12})_s$— contain one to three heteroatoms independently selected from —O— and —$S(O)_n$—; wherein each of said $R^3$ group members $(C_3$–$C_{12})$cycloalkyl$(CR^{11}R^{12})_s$—, $(C_6$–$C_{10})$aryl-$(CR^{11}R^{12})_q$—$(CH_2)$—, $(C_1$–$C_{10})$heterocyclyl $(CR^{11}R^{12})_s$— and $(C_1$–$C_{10})$heteroaryl$(CR^{11}R^{12})_s$— may optionally be substituted on any ring carbon atom able to support an additional substituent, by one to four substituents per ring, independently selected from the group consisting of halo, hydroxy, —CN, $(C_1$–$C_4)$ alkyl, $(C_1$–$C_4)$alkoxy, —$CF_3$, $CF_3O$—, $(C_1$–$C_4)$alkyl-S—, $(C_1$–$C_4)$alkyl-(S=O)—, $(C_1$–$C_4)$alkyl-$(SO_2)$—, $(C_1$–$C_4)$alkyl-O—(C=O)—, formyl, $(C_1$–$C_4)$alkyl-(C=O)—, $(C_8$–$C_{10})$aryl, $[(C_8$–$C_{10})aryl]_2$-CH—, $(C_3$–$C_8)$cycloalkyl, $(C_1$–$C_{10})$heteroaryl, $(C_1$–$C_{10})$heterocyclyl, $(C_6$–$C_{10})$aryl-O—, benzyl-O—, $(C_3$–$C_8)$cycloalkyl-O—, $(C_1$–$C_{10})$heteroaryl-O— and $(C_1$–$C_{10})$ heterocyclyl-O—; wherein said $R^3$ group members $(C_3$–$C_8)$cycloalkyl$(CR^{11}R^{12})_s$— and $(C_1$–$C_{10})$heterocyclyl$(CR^{11}R^{12})_s$— may also optionally be substituted by oxo; wherein each of the aforesaid $(C_6$–$C_{10})$aryl, $(C_3$–$C_8)$cycloalkyl, $(C_1$–$C_{10})$heteroaryl and $(C_1$–$C_{10})$ heterocyclyl anywhere on said $R^3$ substituents may optionally be substituted on any ring carbon atom by one to three moieties per ring, independently selected from the group consisting of halo, hydroxy, amino, —CN, $(C_1$–$C_4)$alkyl, $(C_1$–$C_4)$alkoxy, —$CF_3$, $CF_3O$—, $(C_1$–$C_4)$alkyl-NH—, $[(C_1$–$C_4)alkyl]_2$-N—, $(C_1$–$C_4)$ alkyl-S—, $(C_1$–$C_4)$alkyl-(S=O)—, $(C_1$–$C_4)$alkyl-$(SO_2)$—, $(C_1$–$C_4)$alkyl-O—(C=O)—, formyl, and $(C_1$–$C_4)$alkyl-(C=O)—;

$R^6$, $R^7$ and $R^8$ are each independently selected from the group consisting of hydrogen, halogen, cyano, hydroxyl, $(C_1$–$C_6)$alkyl optionally substituted by one to four chloro or fluoro, and $(C_1$–$C_6)$alkyloxy optionally substituted by one to four chloro or fluoro;

$R^{11}$ and $R^{12}$ are each independently selected from the group consisting of hydrogen, fluoro, cyano, hydroxyl, —$CF_3$, $CF_3O$—, $(C_1$–$C_6)$alkyl, $(C_3$–$C_8)$cycloalkyl, $(C_1$–$C_6)$alkyloxy, $(C_3$–$C_8)$cycloalkyloxy, phenyl, $(C_1$–$C_{10})$heteroaryl and $(C_1$–$C_{10})$heterocyclyl; wherein said $(C_1$–$C_6)$alkyl, $(C_3$–$C_8)$cycloalkyl, $(C_1$–$C_6)$alkyloxy, $(C_3$–$C_8)$cycloalkyloxy phenyl, $(C_1$–$C_{10})$heteroaryl and $(C_1$–$C_{10})$heterocyclyl may optionally be substituted by one to three substituents independently selected from chloro, fluoro, cyano, hydroxyl, —$CF_3$, $CF_3O$—, $(C_1$–$C_4)$alkyl-S—, $(C_1$–$C_4)$alkyl-(S=O)—, $(C_1$–$C_4)$alkyl-$(SO_2)$—, $(C_1$–$C_4)$alkyl-O—(C=O)—, formyl, or $(C_1$–$C_4)$alkyl-(C=O)—, with the proviso that when said $R^3$ is $(C_3$–$C_{12})$cycloalkyl$(CR^{11}R^{12})_s$—; $R^1$ and $R^2$ are each hydrogen; and s is one or two; then said $(C_3$–$C_{12})$cycloalkyl must be other than optionally substituted adamantyl;

or a pharmaceutically acceptable salt thereof.

2. A compound according to claim 1 wherein X, Y and Z are =$(CR^6)$—, =$(CR^7)$—, and =$(CR^8)$—, respectively; and each of $R^6$, $R^7$ and $R^8$ is hydrogen.

3. A compound according to claim 2, wherein A is —(C=O)NH—.

4. A compound according to claim 2, wherein A is —NH(C=O)—.

5. A compound according to claim 3, wherein $R^3$ is $(C_4$–$C_{10})$alkyl.

6. A compound according to claim 3, wherein $R^3$ is $(C_4$–$C_{10})$alkyl substituted with one to three substituents independently selected from halo, hydroxy, —CN, $(C_1$–$C_4)$ alkyl, $(C_1$–$C_4)$alkoxy, —$CF_3$, $CF_3O$—, $(C_1$–$C_4)$alkyl-S—, $(C_1$–$C_4)$alkyl-(S=O)—, $(C_1$–$C_4)$alkyl-$(SO_2)$—, $(C_1$–$C_4)$alkyl-O—(C=O)—, formyl, and $(C_1$–$C_4)$alkyl-(C=O)—.

7. A compound according to claim 3, wherein $R^3$ is $(C_3$–$C_{12})$cycloalkyl-$(CR^{11}R^{12})_s$— wherein $R^{11}$ and $R^{12}$ are each independently hydrogen or $(C_1$–$C_4)$alkyl.

8. A compound according to claim 3, wherein $R^3$ is $(C_3$–$C_{12})$cycloalkyl-$(CR^{11}R^{12})_s$— wherein at least one of $R^{11}$ and $R^{12}$ is other than hydrogen or $(C_1$–$C_4)$alkyl.

9. A compound according to claim 3, wherein $R^3$ is $(C_3$–$C_{12})$cycloalkyl-$(CR^{11}R^{12})_s$— optionally substituted by one to three substituents independently selected from the group consisting of hydrogen, halo, hydroxy, —CN, $(C_1$–$C_4)$alkyl, $(C_1$–$C_4)$alkoxy, oxo, —$CO_2$—$(C_1$–$C_4)$alkyl, formyl, and $(C_1$–$C_4)$alkyl-(C=O)—.

10. A compound according to claim 3, wherein $R^3$ is $(C_3$–$C_{12})$cycloalkyl-$(CR^{11}R^{12})_s$— optionally substituted by one to three substituents independently selected from the group consisting of hydrogen, halo, hydroxy, —CN, $(C_1$–$C_4)$alkyl and $(C_1$–$C_4)$alkoxy.

11. A compound according to claim 3, wherein $R^3$ is $(C_3$–$C_{12})$cycloalkyl-$(CR^{11}R^{12})_s$— optionally substituted by at least one substituent selected from the group consisting of $(C_6$–$C_{10})$aryl, $(C_3$–$C_8)$cycloalkyl, $(C_1$–$C_{10})$heteroaryl, $(C_1$–$C_{10})$heterocyclyl, $(C_6$–$C_{10})$aryl-O—, $(C_3$–$C_8)$cycloalkyl-O—, $(C_1$–$C_{10})$heteroaryl-O— and $(C_1$–$C_{10})$heterocyclyl-O—; wherein each of the aforesaid $(C_6$–$C_{10})$aryl, $(C_3$–$C_8)$cycloalkyl, $(C_1$–$C_{10})$heteroaryl and $(C_1$–$C_{10})$heterocyclyl anywhere on said $(C_3$–$C_{12})$cycloalkyl-$(CR^{11}R^{12})_s$— substituents may optionally be substituted by one to three moieties per ring, independently selected from the group consisting of halo, hydroxy, —CN, $(C_1$–$C_4)$alkyl, $(C_1$–$C_4)$ alkoxy, —$CF_3$, $CF_3O$—, $(C_1$–$C_4)$alkyl-S—, $(C_1$–$C_4)$alkyl-(S=O)—, $(C_1$–$C_4)$alkyl-$(SO_2)$—, —$CO_2$—$(C_1$–$C_4)$alkyl, formyl, and $(C_1$–$C_4)$alkyl-(C=O)—.

12. A compound according to claim 3, wherein $R^3$ is $(C_3$–$C_{12})$cycloalkyl-$(CR^{11}R^{12})_s$— optionally substituted by at least one spiro substituent selected from the group consisting of $(C_6$–$C_{10})$aryl, $(C_3$–$C_8)$cycloalkyl, $(C_1$–$C_{10})$heteroaryl, $(C_1$–$C_{10})$heterocyclyl, $(C_6$–$C_{10})$aryl-O—, $(C_3$–$C_8)$ cycloalkyl-O—, $(C_1$–$C_{10})$heteroaryl-O— and $(C_1$–$C_{10})$ heterocyclyl-O—; wherein each of the aforesaid $(C_6$–$C_{10})$ aryl, $(C_3$–$C_8)$cycloalkyl, $(C_1$–$C_{10})$heteroaryl and $(C_1$–$C_{10})$ heterocyclyl spiro substituent on said $(C_3$–$C_{12})$cycloalkyl-$(CR^{11}R^{12})_s$— may optionally be substituted by one to three moieties per ring, independently selected from the group consisting of halo, hydroxy, —CN, $(C_1$–$C_4)$alkyl, $(C_1$–$C_4)$ alkoxy, —$CF_3$, $CF_3O$—, $(C_1$–$C_4)$alkyl-S—, $(C_1$–$C_4)$alkyl-(S=O)—, $(C_1$–$C_4)$alkyl-$(SO_2)$—, —$CO_2$—$(C_1$–$C_4)$alkyl, formyl, and $(C_1$–$C_4)$alkyl-(C=O)—.

13. A compound according to claim 3, wherein $R^3$ is $(C_6$–$C_{10})$aryl-$(CR^{11}R^{12})_q$—$(CH_2)$—; wherein $R^{11}$ and $R^{12}$ are each independently hydrogen or $(C_1$–$C_4)$alkyl.

14. A compound according to claim 3, wherein $R^3$ is $(C_6$–$C_{10})$aryl-$(CR^{11}R^{12})_q$—$(CH_2)$—; wherein $R^{11}$ and $R^{12}$ are each independently selected from the group consisting of hydrogen and $(C_1$–$C_4)$alkyl and wherein each of $R^{11}$ and $R^{12}$ of the $CR^{11}R^{12}$ directly attached to group A are hydrogen;

and wherein said $(C_6-C_{10})$aryl of said $(C_6-C_{10})$aryl-$(CR^{11}R^{12})_q$—$(CH_2)$— group member is substituted by one to three substituents independently selected from the group consisting of hydrogen, halo, hydroxy, —CN, $(C_1-C_4)$alkyl, $(C_1-C_4)$alkoxy, oxo, $(C_1-C_4)$alkyl-O—(C=O)—, formyl, benzyloxy and $(C_1-C_4)$alkyl-(C=O)—.

15. A compound according to claim 3, wherein $R^3$ is $(C_6-C_{10})$aryl-$(CR^{11}R^{12})_q$—$(CH_2)$—; wherein $R^{11}$ and $R^{12}$ are each independently selected from the group consisting of hydrogen and $(C_1-C_4)$alkyl; and wherein said $(C_6-C_{10})$aryl of said $(C_6-C_{10})$aryl-$(CR^{11}R^{12})_q$—$(CH_2)$— group member is substituted by one to three substituents independently selected from the group consisting of hydrogen, halo, —CN, $(C_1-C_4)$alkyl, benzyloxy and $(C_1-C_4)$alkoxy.

16. A compound according to claim 3, wherein $R^3$ is $(C_6-C_{10})$aryl-$(CR^{11}R^{12})_q$—$(CH_2)$—; wherein $R^{11}$ and $R^{12}$ are each independently selected from the group consisting of hydrogen and $(C_1-C_4)$alkyl; and wherein said $(C_6-C_{10})$aryl of said $(C_6-C_{10})$aryl-$(CR^{11}R^{12})_q$—$(CH_2)$— group member is substituted by at least one substituent selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein each of the aforesaid $(C_6-C_{10})$aryl, $(C_3-C_8)$cycloalkyl, $(C_1-C_{10})$heteroaryl and $(C_1-C_{10})$heterocyclyl substituents may optionally be substituted by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, benzyloxy and $(C_1-C_4)$alkyl-(C=O)—.

17. A compound according to claim 3, wherein $R^3$ is $(C_1-C_{10})$heteroaryl-$(CR^{11}R^{12})_s$— optionally substituted on any carbon atom able to support an additional substituent by one to three substituents per ring independently selected from the group consisting of halo, hydroxy, —CN, $(C_1-C_4)$alkyl, $(C_1-C_4)$alkoxy, $(C_1-C_4)$alkyl-O—(C=O)—, formyl, and $(C_1-C_4)$alkyl-(C=O)—.

18. A compound according to claim 3, wherein $R^3$ is $(C_1-C_{10})$heteroaryl-$(CR^{11}R^{12})_s$— optionally substituted on any carbon atom able to support an additional substituent by one to three substituents per ring independently selected from the group consisting of halo, —CN, $(C_1-C_4)$alkyl, $(C_1-C_4)$alkoxy, formyl, and $(C_1-C_4)$alkyl-(C=O)—.

19. A compound according to claim 3, wherein $R^3$ is $(C_1-C_{10})$heteroaryl-$(CR^{11}R^{12})_s$— optionally substituted on at least one carbon atom able to support an additional substituent by a substituent selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein the aforesaid $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O— substituents may optionally be substituted on any ring carbon atom by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

20. A compound according to claim 3, wherein $R^3$ is $(C_1-C_{10})$heterocyclyl-$(CR^{11}R^{12})_s$— optionally substituted on any carbon atom able to support an additional substituent by one to three substituents per ring independently selected from the group consisting of halo, hydroxy, —CN, $(C_1-C_4)$alkyl, $(C_1-C_4)$alkoxy, oxo, $(C_1-C_4)$alkyl-O—(C=O)—, formyl, and $(C_1-C_4)$alkyl-(C=O)—.

21. A compound according to claim 3, wherein $R^3$ is $(C_1-C_{10})$heterocyclyl-$(CR^{11}R^{12})_s$— optionally substituted on any carbon atom able to support an additional substituent by one to three substituents per ring independently selected from the group consisting of halo, —CN, $(C_1-C_4)$alkyl, $(C_1-C_4)$alkoxy, oxo, formyl, and $(C_1-C_4)$alkyl-(C=O)—.

22. A compound according to claim 3, wherein $R^3$ is $(C_1-C_{10})$heterocyclyl-$(CR^{11}R^{12})_s$— optionally substituted on at least one carbon atom able to support an additional substituent by a substituent selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein the aforesaid $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O— substituents may optionally be substituted on any ring carbon atom by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

23. A compound according to claim 3, wherein $R^3$ is $(C_1-C_{10})$heterocyclyl-$(CR^{11}R^{12})_s$— optionally substituted on at least one carbon atom able to support an additional substituent by a spiro substituent selected from the group consisting of $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O—; wherein the aforesaid $(C_6-C_{10})$aryl, $(C_3-C_8)$cycloalkyl, $(C_1-C_{10})$heteroaryl, $(C_1-C_{10})$heterocyclyl, $(C_6-C_{10})$aryl-O—, $(C_3-C_8)$cycloalkyl-O—, $(C_1-C_{10})$heteroaryl-O— and $(C_1-C_{10})$heterocyclyl-O— spiro substituents may optionally be substituted on any ring carbon atom by one to three moieties per ring, independently selected from the group consisting of halo, hydroxy, —CN, $(C_1-C_4)$alkyl, $(C_1-C_4)$alkoxy, —CF$_3$, CF$_3$O—, $(C_1-C_4)$alkyl-S—, $(C_1-C_4)$alkyl-(S=O)—, $(C_1-C_4)$alkyl-(SO$_2$)—, $(C_1-C_4)$alkyl-O—(C=O)—, formyl, and $(C_1-C_4)$alkyl-(C=O)—.

24. A compound according to claim 2, wherein $R^2$ is chloro or bromo.

25. A compound according to claim 2, wherein $R^2$ is chloro.

26. A compound according to claim 2, wherein $R^2$ is $(C_1-C_4)$alkyl or —CN.

27. A compound according to claim 2, wherein $R^2$ is hydroxy.

28. A compound according to claim 1, wherein $R^7$ is other than hydrogen.

29. A compound according to claim 1, wherein said compound is 2-Chloro-N-[2-(2-chloro-phenyl)-ethyl]-5-(3-oxo-2,3-dihydro-benzo[1,4]thiazin-4-yl)-benzamide or a pharmaceutically acceptable salt thereof.

30. A method for treating arthritis in a mammal comprising administering to said mammal an amount of a compound according to claim 1, effective in treating arthritis.

31. A pharmaceutical composition for the treatment of arthritis in a mammal-comprising an amount of a compound according to claim 1, effective in treating arthritis and a pharmaceutically acceptable carrier.

* * * * *